United States Patent
Paul et al.

(10) Patent No.: US 8,021,361 B2
(45) Date of Patent: Sep. 20, 2011

(54) SYSTEMS AND METHODS FOR ELECTRODE CONTACT ASSESSMENT

(75) Inventors: Saurav Paul, Minnetonka, MN (US); Troy Tegg, Elk River, MN (US); Chou Thao, Brooklyn Park, MN (US); Hong Cao, Savage, MN (US); Harry A. Puryear, Shoreview, MN (US); Fos Kuehn, Richfield, MN (US); Reed R. Heimbecher, Medina, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 697 days.

(21) Appl. No.: 11/553,965

(22) Filed: Oct. 27, 2006

(65) Prior Publication Data

US 2007/0100332 A1    May 3, 2007

Related U.S. Application Data

(60) Provisional application No. 60/730,634, filed on Oct. 27, 2005.

(51) Int. Cl.
    *A61B 18/14* (2006.01)
(52) U.S. Cl. ............................................. 606/41; 606/42
(58) Field of Classification Search ................ 606/41–48
    See application file for complete search history.

(56) References Cited

U.S. PATENT DOCUMENTS

| | | | |
|---|---|---|---|
| 4,600,017 A | 7/1986 | Schroeppel | |
| 4,682,596 A * | 7/1987 | Bales et al. | ...................... 606/39 |
| 4,799,495 A | 1/1989 | Hawkins et al. | |
| 4,911,174 A | 3/1990 | Pederson et al. | |
| 4,976,711 A | 12/1990 | Parins et al. | |
| 4,991,588 A | 2/1991 | Pflueger et al. | |
| 5,028,394 A | 7/1991 | Lowell, Jr. et al. | |
| 5,327,905 A * | 7/1994 | Avitall | .......................... 600/585 |
| 5,341,807 A | 8/1994 | Nardella | |
| 5,354,279 A | 10/1994 | Höfling | |
| 5,372,603 A | 12/1994 | Acker et al. | |
| 5,396,887 A | 3/1995 | Imran | |

(Continued)

FOREIGN PATENT DOCUMENTS

EP    1491139    12/2004

(Continued)

OTHER PUBLICATIONS

Olaf J. Eick, et al., "The LETR-Principle: A Novel Method to Assess Electrode-Tissue Contact in Radiofrequency Ablation," Jul. 1998.

(Continued)

*Primary Examiner* — Linda C Dvorak
*Assistant Examiner* — Amanda Scott
(74) *Attorney, Agent, or Firm* — Trenner Law Firm, LLC

(57) ABSTRACT

Systems and methods are disclosed for assessing electrode-tissue contact for tissue ablation. An exemplary electrode contact sensing system comprises an electrode housed within a distal portion of a catheter shaft. At least one electro-mechanical sensor is operatively associated with the electrode within the catheter shaft. The at least one electro-mechanical sensor is responsive to movement of the electrode by generating electrical signals corresponding to the amount of movement. The system may also include an output device electrically connected to the at least one electro-mechanical sensor. The output device receives the electrical signals for assessing a level of contact between the electrode and a tissue.

18 Claims, 28 Drawing Sheets

U.S. PATENT DOCUMENTS

| | | | | |
|---|---|---|---|---|
| 5,405,346 | A * | 4/1995 | Grundy et al. | 606/41 |
| 5,447,529 | A | 9/1995 | Marchlinski | |
| 5,536,245 | A | 7/1996 | Dahlbeck | |
| 5,545,161 | A * | 8/1996 | Imran | 606/41 |
| 5,643,197 | A | 7/1997 | Brucker et al. | |
| 5,697,925 | A | 12/1997 | Taylor | |
| 5,782,828 | A * | 7/1998 | Chen et al. | 606/42 |
| 5,836,990 | A | 11/1998 | Li | |
| 5,868,737 | A | 2/1999 | Taylor et al. | |
| 5,893,848 | A | 4/1999 | Negus et al. | |
| 5,895,355 | A | 4/1999 | Schaer et al. | |
| 5,947,905 | A | 9/1999 | Hadjicostis et al. | |
| 6,013,074 | A | 1/2000 | Taylor | |
| 6,039,731 | A | 3/2000 | Taylor et al. | |
| 6,066,139 | A | 5/2000 | Ryan et al. | |
| 6,078,830 | A | 6/2000 | Levin et al. | |
| 6,113,592 | A | 9/2000 | Taylor | |
| 6,113,593 | A * | 9/2000 | Tu et al. | 606/34 |
| 6,127,672 | A | 10/2000 | Danisch | |
| 6,171,304 | B1 | 1/2001 | Netherly et al. | |
| 6,210,406 | B1 | 4/2001 | Webster | |
| 6,217,573 | B1 | 4/2001 | Webster | |
| 6,217,574 | B1 | 4/2001 | Webster | |
| 6,241,724 | B1 * | 6/2001 | Fleischman et al. | 606/41 |
| 6,246,898 | B1 | 6/2001 | Vesely et al. | |
| 6,264,653 | B1 | 7/2001 | Falwell | |
| 6,272,371 | B1 | 8/2001 | Shlomo | |
| 6,304,776 | B1 | 10/2001 | Muntermann | |
| 6,322,558 | B1 | 11/2001 | Taylor et al. | |
| 6,325,799 | B1 | 12/2001 | Goble | |
| 6,391,024 | B1 | 5/2002 | Sun et al. | |
| 6,423,057 | B1 | 7/2002 | He et al. | |
| 6,470,236 | B2 * | 10/2002 | Ohtsuki | 700/247 |
| 6,696,844 | B2 | 2/2004 | Wong et al. | |
| 6,800,986 | B2 | 10/2004 | Yamauchi | |
| 6,837,886 | B2 | 1/2005 | Collins et al. | |
| 6,845,264 | B1 | 1/2005 | Skladnev et al. | |
| 6,882,885 | B2 | 4/2005 | Levy, Jr. et al. | |
| 7,011,410 | B2 | 3/2006 | Bolger et al. | |
| 7,060,965 | B2 | 6/2006 | Vidovic et al. | |
| 2001/0034501 | A1 * | 10/2001 | Tom | 604/67 |
| 2002/0123749 | A1 * | 9/2002 | Jain | 606/41 |
| 2003/0056351 | A1 * | 3/2003 | Wilkie et al. | 29/25.35 |
| 2003/0130615 | A1 | 7/2003 | Tom | |
| 2003/0204184 | A1 | 10/2003 | Ferek-Patric | |
| 2004/0199156 | A1 * | 10/2004 | Rioux et al. | 606/41 |
| 2004/0210214 | A1 | 10/2004 | Knowlton | |
| 2004/0217674 | A1 * | 11/2004 | Bianchini | 310/365 |
| 2005/0159739 | A1 | 7/2005 | Paul et al. | |
| 2005/0159741 | A1 | 7/2005 | Paul et al. | |
| 2005/0267467 | A1 | 12/2005 | Paul et al. | |
| 2007/0078484 | A1 | 4/2007 | Talarico et al. | |
| 2008/0255629 | A1 * | 10/2008 | Jenson et al. | 607/19 |
| 2008/0275442 | A1 | 11/2008 | Paul et al. | |
| 2009/0158852 | A1 | 6/2009 | Paul et al. | |

FOREIGN PATENT DOCUMENTS

| | | |
|---|---|---|
| EP | 1491139 A2 | 12/2004 |
| WO | WO-95/10978 | 4/1995 |
| WO | WO-98/17185 | 4/1998 |
| WO | WO-2004/098694 | 11/2004 |
| WO | 2005039835 A1 | 5/2005 |
| WO | WO2005039835 | 5/2005 |

OTHER PUBLICATIONS

Measurement Specialties, Inc., "Piezo Film Sensors Technical Manual," Apr. 1999.

PCT International Search Report and Written Opinion of the International Searching Authority for PCT/US07/80981, dated Apr. 16, 2008, 9 pages.

PCT International Search Report and Written Opinion of the International Searching Authority for PCT/US07/80983 dated Apr. 2, 2008, 8 pages.

Biopac Systems, Inc., "Micro Pressure Measurement System—Product Overview," 39 pages.

"Fiber Optic Interferometer Fabry-Perot," available from http://physics.nad.ru/Physics/English/ifp_txt.htm at least as early as Oct. 15, 2007, 5 pages.

Medical Product Manufacturing News "Need to Know," 1 page, Sep. 2007.

BIOSEB: Samba—Blood Pressure System, available from http://www.bioseb.com/anglais/default/item_id=904_cat_id=3+Samba%20-%20Blood%20Pressure%System.php at least as early as Oct. 15, 2007, 4 pages.

Samba Sensors, "The Samba Technology," available from http://www.samba.se/index2.cfm?PageID=45 at least as early as Oct. 15, 2007, 1 page.

Samba Sensors, "Publications related to Samba Sensors AB," 3 pages.

PCT International Search Report and Written Opinion of the International Searching Authority for PCT/US06/39881, dated Jun. 30, 2008, 7 pages.

PCT International Search Report and Written Opinion of the International Searching Authority for PCT/US06/42119, dated Sep.13, 2007, 9 pages.

* cited by examiner

SYSTEMS AND METHODS FOR ELECTRODE CONTACT ASSESSMENT

CROSS-REFERENCE TO RELATED APPLICATIONS

This application claims the benefit of U.S. provisional application No. 60/730,634 filled 27 Oct. 2005, which is hereby incorporated by reference as though fully set forth herein.

BACKGROUND OF THE INVENTION a. Field of the Invention

The instant invention is directed toward an electrode catheter and a method for using the electrode catheter for tissue ablation. In particular, the electrode catheter of the present invention may comprise one or more electro-mechanical sensors such as a piezoelectric sensor for assessing catheter contact with a moving surface (e.g., the heart wall) for ablation procedures.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, lesions may be formed at specific locations in cardiac tissue via coagulation necrosis to lessen or eliminate undesirable atrial fibrillations.

Several difficulties may be encountered, however, when attempting to form lesions at specific locations using some existing ablation electrodes. One such difficulty encountered with existing ablation electrodes is how to assess tissue contact. Electrode-tissue contact is not readily determined using conventional fluoroscopy techniques. Instead, the physician determines electrode-tissue contact based on his/her experience using the electrode catheter. Such experience only comes when time, and may be quickly lost if the physician does not use the electrode catheter on a regular basis. In addition, when forming lesions in a heart, the beating of the heart further complicates matters, making it difficult to assess and maintain sufficient contact pressure between the electrode and the tissue for a sufficient length of time to form a desired lesion. If the contact between the catheter and the tissue cannot be properly maintained, a quality lesion is unlikely to be formed.

BRIEF SUMMARY OF THE INVENTION

It is desirable to be able to assess electrode contact with a surface (e.g., the heart wall) for tissue ablation procedures. Positioning the electrode against the heart will creates contact stresses between the electrode and the tissue. This stress may be measured by implementing one or more electro-mechanical sensors, such as a piezoelectric sensor, coupled to the electrode. The piezoelectric sensor(s) generates a voltage signal and charge corresponding to stress of the electrode.

In an exemplary embodiment, a piezoelectric sensor is operatively associated with an electrode housed within a catheter shaft. In another exemplary embodiment, a plurality piezoelectric sensors are provided within the electrode catheter. Output from the piezoelectric sensor(s) enable a user (e.g., a physician or technician) to position the electrode catheter against a target tissue with the desired amount of pressure for the ablation procedure.

An exemplary electrode contact sensing system may comprise an electrode housed within a distal portion of a catheter shaft. At least one piezoelectric sensor is operatively associated with the electrode within the catheter shaft. The at least one piezoelectric sensor is responsive to stress of the electrode by generating electrical signals corresponding to the amount of stress. The system may also include an output device electrically connected to the at least one piezoelectric sensor. The output device receives the electrical signals for assessing a level of contact between the electrode and a tissue.

An exemplary method of assessing electrode-tissue contact for tissue ablation may comprise: generating piezoelectric signals in response to stress of an electrode housed within a distal portion of a flexible catheter, and assessing a level of contact between the electrode and a moving tissue based on the piezoelectric signals.

Output may be conveyed to the user in real-time (e.g., at a display device or other interface) so that the user can properly position the electrode on the target tissue with the desired level of contact for the ablation procedure. For example, the user may increase contact pressure if the output indicates insufficient contact. Or for example, the user may reduce contact pressure if the output indicates too much contact.

The foregoing and other aspects, features details utilities, and advantages of the present invention will be apparent from reading the following description and claims, and from reviewing the accompanying drawings.

BRIEF DESCRIPTION OF THE DRAWINGS

FIG. 10b-j are cross-sectional views showing alternative embodiments of the piezoelectric sensor shown in FIG. 10a.

DETAILED DESCRIPTION OF THE INVENTION

Exemplary embodiments of a tissue ablation system and methods of use to assess contact between an electrode in catheter and a tissue are depicted in the figures. Exemplary system comprise an electrode which may be inserted into the patient using a catheter, e.g., for forming ablative lesions inside the patients heart. During an exemplary ablation procedure, a user (e.g., the patient's physician or a technician) may insert the catheter into one of the patient's blood vessels, e.g., through the leg or the patient's neck. The user, guided by a real-time fluoroscopy imaging device, moves the catheter into the patient's heart.

When the catheter reaches the patient's heart, electrodes at the distal portion of the catheter may be implemented to electrically map the myocardium (i.e., muscular tissue in the heart wall) and locate a target tissue. After locating the target tissue, the user must move the catheter into contact with the target tissue before applying ablative energy from the same or other electrodes in the catheter to form an ablative lesion or lesions. The level of contact is often critical to form sufficiently deep ablative lesions on the target tissue without damaging surrounding tissue in the heart.

As described further below, the system may include one or more electro-mechanical sensors, such as a piezoelectric sensor, which generate electric signals in response to the electrode coming into contract with a surface (e.g., target tissue within the beating heart) Accordingly, embodiments of the present invention provide a number of advantages, including, for example, the ability, to apply a reasonable amount of ablative energy to a target tissue while mitigating tissue contact problems. The invention also facilitates enhanced tissue contact in difficult environments (e.g., during lesion formation on a moving surface inside a beating heart).

Figure 1A:
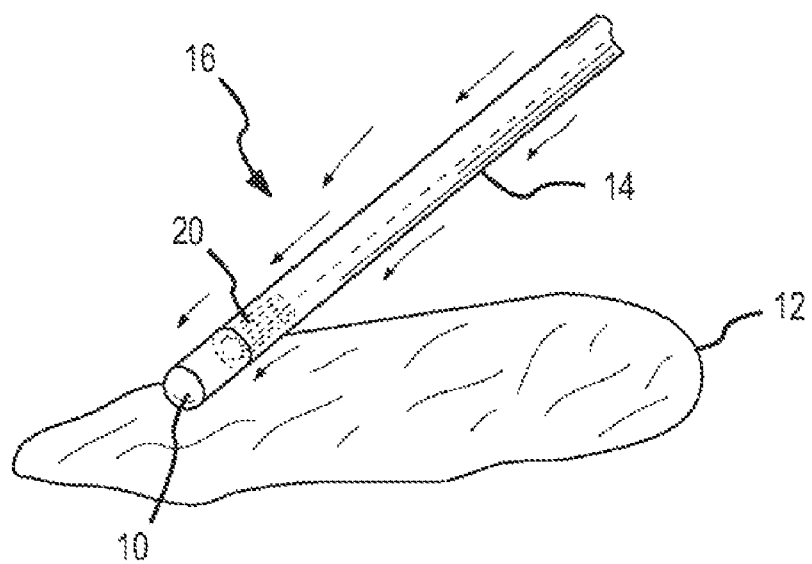
FIG. 1a-b illustrate exemplary contact between an electrode and a moving target tissue.
Figure 1B:
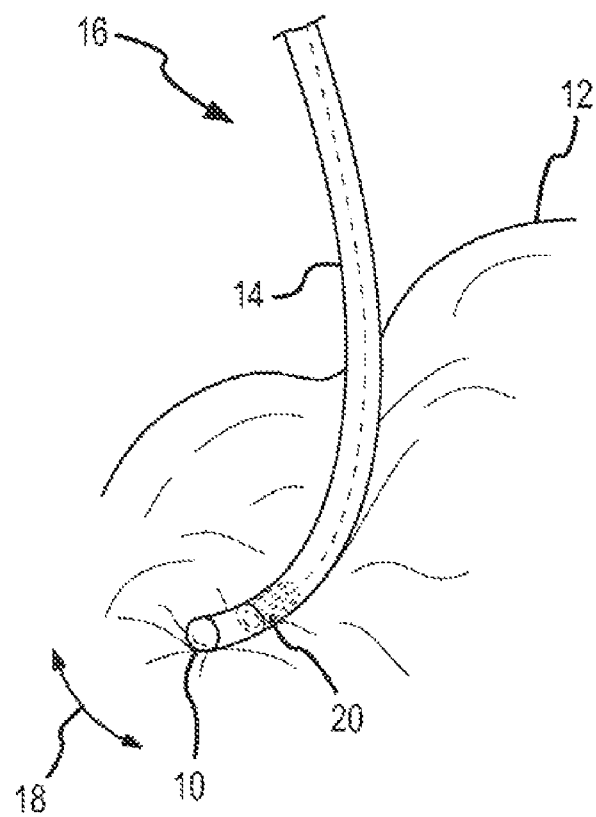

FIG. 1a and 1b illustrate exemplary contact between an electrode 10 and a target tissue 12 (e.g., myocardium). Electrode 10 may be provided in a flexible shaft 14 of the catheter 16. The flexible catheter shaft 14 may be made of a plastic or other suitable material which enables the electrode 10 to be readily inserted into the patient's heart through the blood vessels, and to be moved or deflected by movement of an adjacent tissue (e.g., target tissue 12).

The electrode 10 may be electrically connected via suitable wiring through the catheter shaft 14 to a generator (not shown), such as, e.g., a radio frequency (RF) generator. The electrode 10 is thus operable to emit electrical energy (e.g., RF current) near the tip of the electrode 10 for forming thermal lesion(s) on the target tissue during ablation procedures.

A user may operate a handle portion (not shown) of the catheter 16 to manually position the electrode 10 inside the patient's heart so that the electrode 10 is in contact with the target tissue 12. In FIG. 1a, the electrode 10 is shown having little, if any, contact with the target tissue 12, e.g., the electrode 10 may be "floating" adjacent the target tissue 12 as the user is positioning the electrode 10 using catheter 16 in the heart for an ablation procedure. In FIG. 1b, the electrode 10 is shown in contact with the target tissue 12.

When the electrode 10 is in sufficient or "good" contact with the target tissue 12, the electrode 10 may be stressed or deflected by contact with the target tissue 12 generally in the directions illustrated by arrows 18. Stress or deflection of the electrode 10 may be measured in real-time using at least one piezoelectric sensor 20 to assess contact between the electrode 10 and the target tissue 12, as described more fully below.

Before continuing, it is noted that the contact and motion illustrated by FIG. 1b is shown for purposes of illustration and is not intended to be limiting. Other contact and motion may also exist and/or be desired by the user. The definition of sufficient or "good" contact may depend at least to some extent on various operating conditions, such as, e.g., the type of target tissue, desired depth of the ablation lesion, and power and duration of the applied RF energy, to name only a few examples.

It is also noted that other components typical of systems which are conventionally implemented for tissue ablation are not shown or described herein for purpose of brevity. Such components may nevertheless also be provided as part of, or for use with, the electrode 10. For example, these systems commonly include or are used in conjunction with an ECG recording system, and/or various controls for performing the ablation procedure. Such components are well understood in the medical devices arts and therefore further explanation is not necessary for a complete understanding of the invention.

Figure 2:
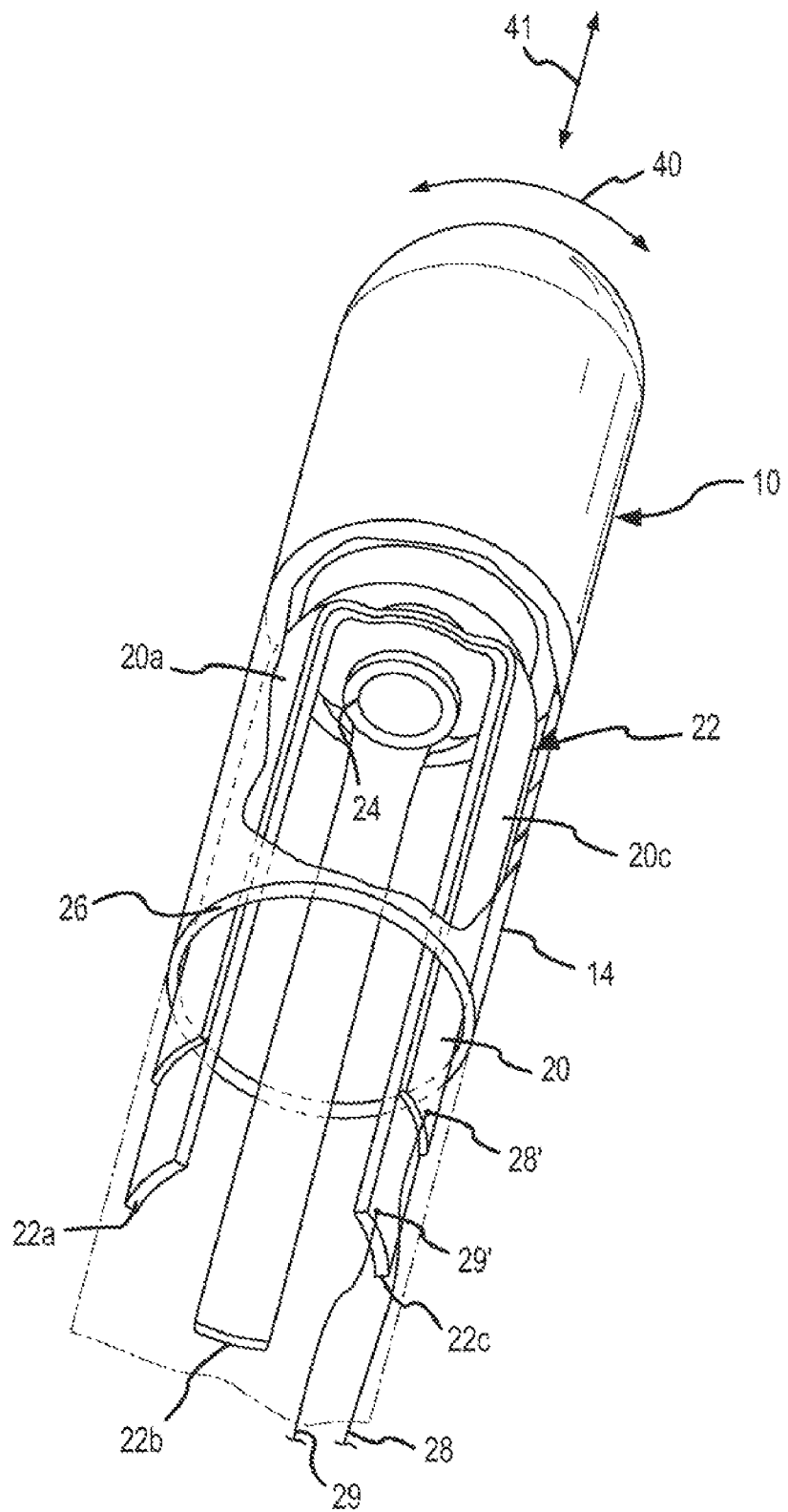
FIG. 2 is perspective view of an exemplary electrode with a piezoelectric sensor.
Figure 2A:
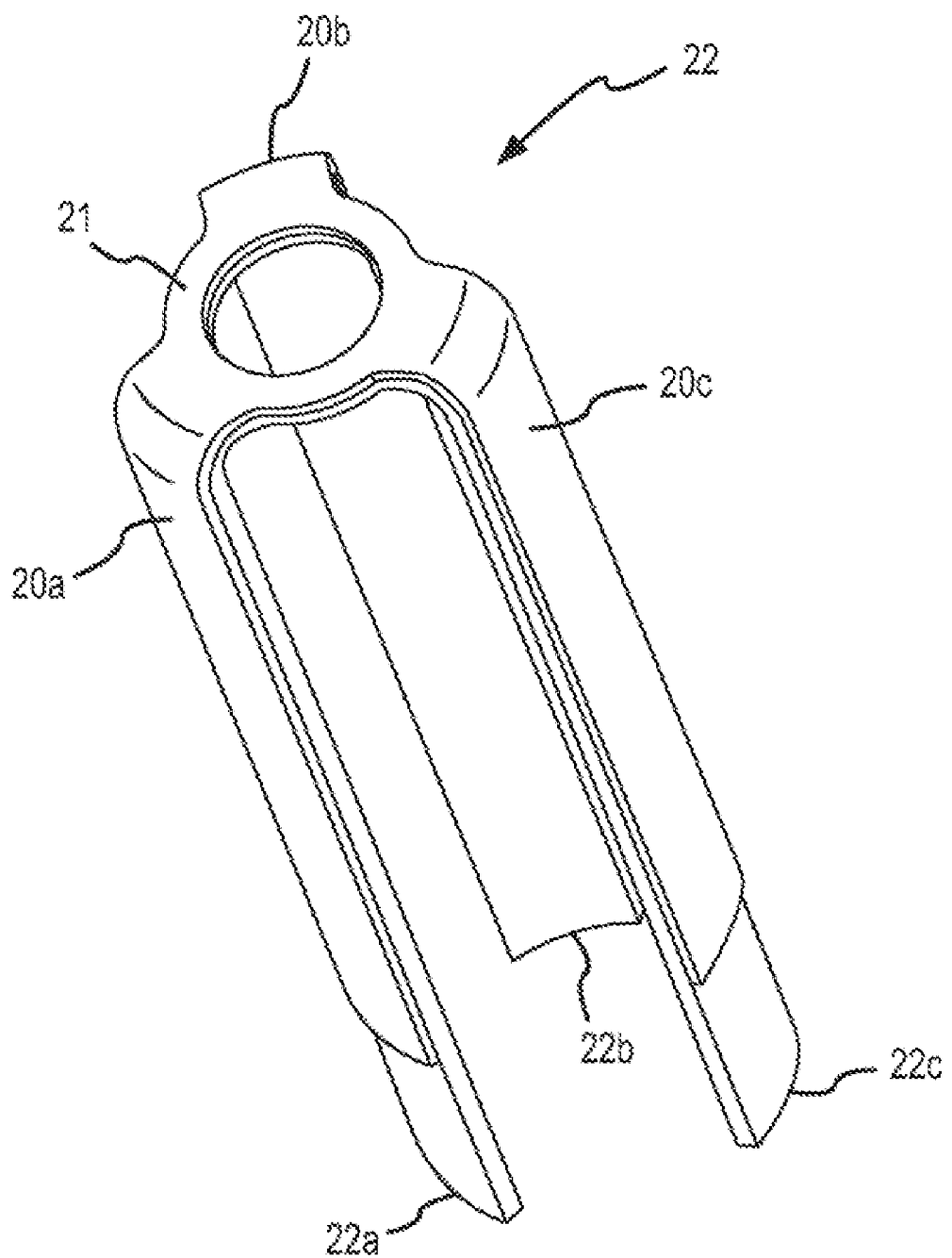
FIG. 2a is a perspective view of an exemplary supporting structure for mounting a piezoelectric sensor to the electrode as shown in FIG. 2.

As previously mentioned, one or more piezoelectric sensors 20 may be operatively associated with the electrode 10 to measure stress of the electrode 10 when in contact with the target tissue 12. FIG. 2 is a perspective view of an exemplary electrode 10 operatively associated with a piezoelectric sensor 20). In this embodiment the piezoelectric sensor 20 is provided on a supporting structure 22 shaped as a tripod. FIG. 2a is a perspective view of an exemplary supporting structure 22 shaped as a tripod with piezoelectric sensor 20 provided thereon. The piezoelectric sensor 20 may be formed as a single piece having arms 20a-c connected by a collar 21 and extending at least partially down each leg 22a-c of the supporting structure 22. The supporting structure 22 is mounted directly to the electrode 20 on neck portion 24, as shown in FIG. 2.

Optionally, the supporting structure 22 with piezoelectric sensor 20 may be provided within an insulated cavity or compliant section 26 of the catheter shaft 14. In addition to housing the piezoelectric sensor 20 in the electrode 10, and protecting the piezoelectric sensor 20 from external damage or corrosion, the compliant section 26 may serve as a low pass mechanical filter. That is, the compliant section 26 attenuates high frequency "noise" signals caused, e.g., by minor vibrations from intermittent contact during positioning of the electrode 10 adjacent the target tissue 12. Accordingly, high frequency noise signals are damped, or even non-existent, as output for the user.

Electrical wiring 28 may be connected to the piezoelectric sensor 20 (e.g., as illustrated by connection 28'). Electrical wiring 29 may also be connected to a around (e.g., as illustrated by connection 29' to the leg 22c of the supporting structure 22 where the supporting structure is an electrical conductor). It is noted that only one wire needs to be connected to the piezoelectric sensor 20 (and one wire to ground) in this embodiment because the piezoelectric sensor 20 is formed as a single piece. The wires 28-29 may extend through the catheter shaft 14 to deliver electrical signals from the piezoelectric sensor 20 to a data acquisition/processing/output device (not shown) such as, e.g., an echocardiogram (ECG) device. Alternatively, a wireless connection may be implemented, e.g., by providing a transmitter in the catheter and a receiver in association with the data acquisition/processing/output device.

In use, the piezoelectric sensor 20 responds to electrode-tissue contact stresses by generating electrical energy (e.g., a voltage or charge). Accordingly, when the electrode 10 is positioned in contact with the target tissue 12, piezoelectric sensor 20 generates an electrical signal corresponding to stress of the electrode 10. The resulting electrical signal may be processed and/or otherwise output for the user so that the user is able to determine when the electrode 10 is positioned with the desired level of contact with the target tissue 12.

Piezoelectric sensors which generate electrical energy in response to applied mechanical stress are well-understood in the electro-mechanical arts. In general, piezoelectric sensors comprise a piezoelectric material which contains positive and negative electrical charges. In a neutral or "non-stressed" state, these electrical charges are symmetrically distributed in the piezoelectric material such that the material exhibits an overall neutral electrical charge. However, subjecting the piezoelectric material to a mechanical stress (e.g., flexure, pressure, and/or tension) disturbs the symmetrical distribution of electrical charges, thereby generating electrical energy across the material. Even minor deformation of some piezoelectric materials (e.g., on the order of nanometers) may generate a measurable voltage signal. Operation of piezoelectric material may be better understood with brief reference to FIG. 3*a-c*

Figure 3A:
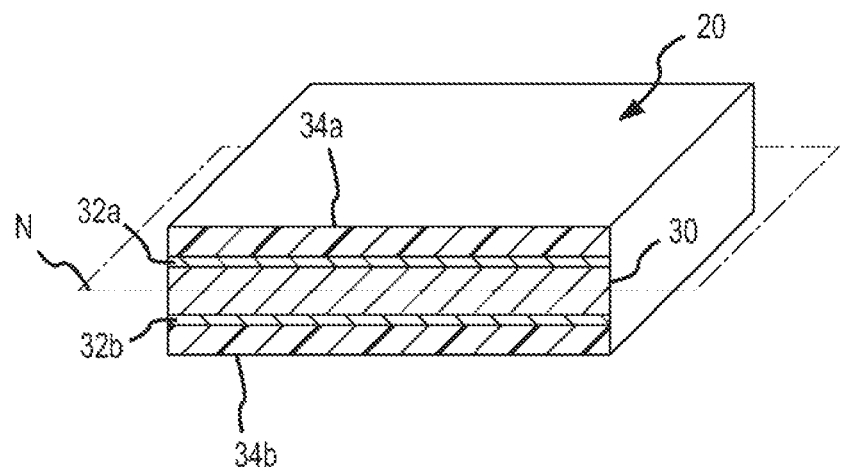
FIG. 3a is a sectional view of an exemplary piezoelectric sensor which may be implemented for use with the electrode.
Figure 3B:
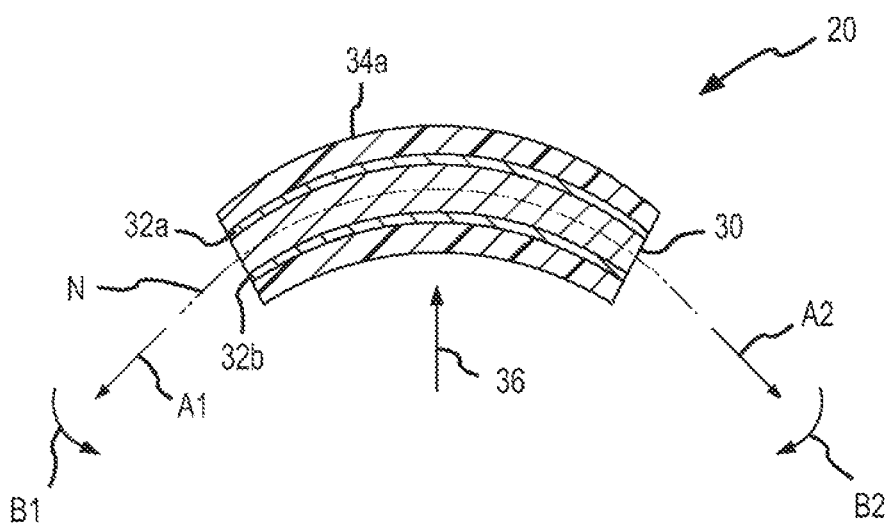
In FIG. 3b-c, the piezoelectric sensor is shown in exaggerated form as it may respond to various stresses.
Figure 3C:
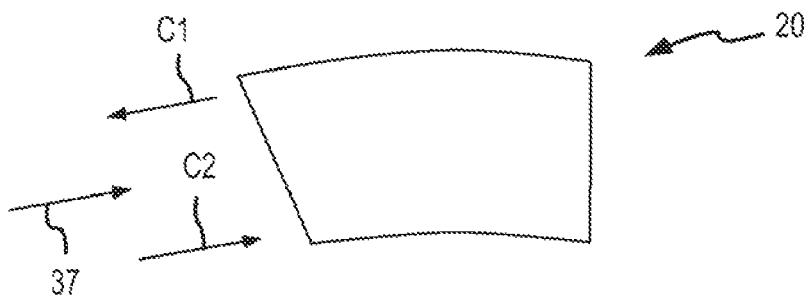

FIG. 3*a* is a cross-sectional perspective view of a portion of an exemplary piezoelectric sensor 20 which may be implemented for use with the electrode 10. In FIG. 3*b-c*, the piezoelectric sensor 20 is shown in exaggerated form as it may respond to various stresses, wherein FIG. 3*b* is a side-view of the piezoelectric sensor 20 in FIG. 3*a*, and FIG. 3*c* is a top-view of the piezoelectric sensor 20 shown in FIG. 3*a*.

In an exemplary embodiment, the piezoelectric sensor 20 may be a laminated sensor, having a plurality of laminated layers. Although not required, laminating the sensor increases it sensitivity. The laminated layers may comprise a piezoelectric material 30 "sandwiched" between metal layers 32*a* and 32*b* and protective coating 34*a* and 34*b*. Metal layers 32*a* and 32*b* may be any suitable metal, e.g., a thin layer of silver ink. The metal layers 32*a* and 32*b* serve to collect electrical charge generated by the piezoelectric material 30, e.g., for delivery as electrical signals via electrical wiring to a data acquisition/processing/output device. Metal layers 32*a* and 32*b* serve to collect electrical energy in response to stress of the piezoelectric material 20. Piezoelectric material, such as PVDF (Kynar), is commercially available as a highly-sensitive, thin, flexible polymer film, which makes it particularly desirable for use with deflectable catheters. Protective coating 34*a* and 34*b* may be any suitable material, e.g., Mylar®.

It is noted that the laminated layers of piezoelectric sensor 20 are not limited to any particular material and/or configuration. For example, the piezoelectric sensor 20 is not limited to use with separate metal layers 32*a* and 32*b*. Nor is the piezoelectric sensor 20 limited to the generally rectangular configuration shown in FIG. 3*a*.

In an exemplary embodiment, the piezoelectric material 30 may comprise a thin, flexible, polymer-based material. One such piezoelectric film is a polyvinylidene fluoride (PVDF) film commercially available from the Sensor Products Division of Measurement Specialties, Inc. (Norristown, Pa.). This PVDF film is approximately 28 μm thick, enabling the PVDF film to be readily housed within the catheter shaft 14.

In addition, this PVDF film has a wire frequency range of about 0.001 Hz to $10^9$ Hz and a high dynamic stress constant ($g_{31}=216\times10^{-3}$ Vm/N). For purposes of illustration, other common piezoelectric materials, such as lead zirconate titanate (PZT) has a dynamic stress constant ($g_{31}$) of $10\times10^{-3}$ Vm/N, and barium titanium oxide ($BaTiO_3$) has a dynamic stress constant ($g_{31}$) of $5\times10^{-3}$ Vm/N. Accordingly, the PVDF film is very sensitive, exhibiting a relatively high voltage response to relatively small mechanical stresses, and is therefore well-suited for measuring dynamic stresses and strains.

Of course, the piezoelectric sensor 20 described above with reference to FIG. 3*a* is for purposes of illustration and not intended to be limiting. Other piezoelectric sensors may also be implemented, and are not limited to laminated piezoelectric film. Nor are piezoelectric sensors limited to use with any particular type or size of piezoelectric material. Selection of piezoelectric sensor 20 for use with the electrode 10 may be application-specific and depend at least in part on one or more design considerations, such as, but not limited to, the desired sensitivity and/or spatial constraints for housing the piezoelectric sensor.

Piezoelectric sensor 20 is shown in FIG. 3*a* in a neutral state. In the neutral state, the piezoelectric material 30 is not subject to any stresses or strains. Accordingly, the electrical charges are symmetrically distributed on either side of the neutral plane N in the piezoelectric material 30 such that the material exhibits an overall neutral electrical charge.

The most widely used coefficients, d3n (for charge) and g3n (for voltage), possess two subscripts. The first refers to the electrical axis, while the second subscript refers to the mechanical axis. Because piezoelectric film is thin, the electrodes are only applied to the top and bottom film surfaces. Accordingly, the electrical axis is always referred to as "3", as the charge or voltage is always transferred through the thickness (n=3) of the film. The mechanical axis can be either 1, 2, or 3, because the stress can be applied to any of these axes. Typically, piezoelectric film is used in the mechanical 1 direction for low frequency sensing and actuation (<100 KHz) and in the mechanical 3 direction for high ultrasound sensing and actuation (>100 KHz). These stresses can be better understood with reference to FIGS. 3*b* and 3*c*.

FIG. 3*b* is a side-view of the piezoelectric sensor 20 shown in FIG. 3*a* in FIG. 3*b*, the piezoelectric sensor 20 is shown in exaggerated from as it may respond to transverse stresses applied generally in the direction of arrow 36. In this stressed state, the piezoelectric material 30 undergoes transverse strain relative to its neutral state, as illustrated by arrows A1 and A2. The piezoelectric sensor 20 may also respond to bending stresses. In this stressed state, the piezoelectric material 30 undergoes flexural strain relative to its neutral state, as illustrated by arrows B1 and B2.

FIG. 3*c* is a top-view of the piezoelectric sensor 20 shown in FIG. 3*a*. In FIG. 3*c*, the piezoelectric sensor 20 is shown in exaggerated form as it may respond to stress distribution applied generally in the direction of arrows 37. In this stressed state, the piezoelectric material 30 is longitudinally strained relative to its neutral state, as illustrated by arrows C1 and C2.

In each case, these stresses disturb the symmetrical distribution of electrical charges, and electrical energy generated across the piezoelectric material 30. In operation, this electrical energy may be collected by metal layers 32*a*, 32*b*, e.g., for delivery as an electrical signal via electrical wiring through the catheter shaft 14 to a signal conditioning/data acquisition/processing/output device (not shown).

Returning to the piezoelectric sensor 20 shown mounted to the electrode 10 in FIG. 2, it can be readily seen that piezoelectric sensor 20 provided on supporting structure 22 and mounted to the electrode 10 is stressed or strained due to stress on the electrode 10 (e.g., in the directions illustrated by arrows 40 and/or 41). The piezoelectric sensor 20 responds by generating electrical (voltage) signals. These electrical signals may be viewed by the user, e.g., as output on an electrical monitoring device.

Figure 4:
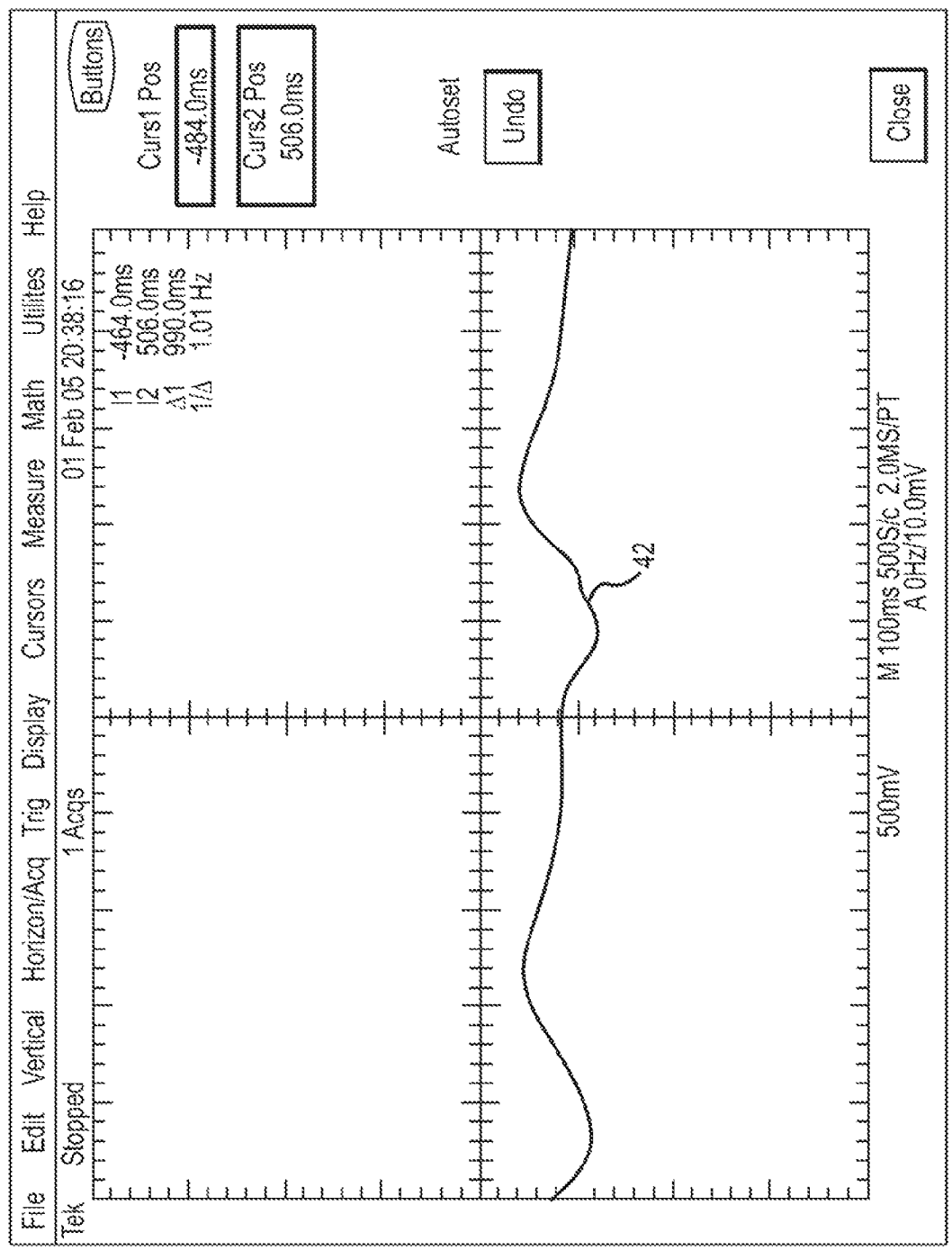
FIG. 4 shows exemplary output of an oscilloscope showing a waveform corresponding to electrical signals generated by a piezoelectric sensor.

FIG. 4 is exemplary output of an oscilloscope showing waveform 40 corresponding to electrical signals generated by a piezoelectric sensor (e.g., piezoelectric sensor 20 in FIG. 2) wherein it is coupled to an electrode in contact with a moving tissue, such as the myocardium. During operation, output such is waveform 42 may be displayed for a user, e.g., as a waveform on an ECG device.

In an exemplary embodiment, the signal strength (e.g., amplitude) from the piezoelectric sensor 20 is proportional to the amount of stress of the electrode 10, and therefore can be used to determine if the electrode 10 is in good contact with a tissue (e.g., the myocardium). If the electrode 10 is not in contact with the target tissue there are no peaks in the resulting waveform 42 (or the peaks are intermittent.) On the other hand, a strong correlation between the heartbeat and output by the piezoelectric sensor indicates that the electrode 10 is in good contact with the moving target tissue.

Signal periodicity is also a strong indicator of dynamic contact assessment. For example, if the period between heartbeats corresponds well with the period output by the piezoelectric sensor 20, the electrode 10 is moving in response to the heartbeat (and not some other reason). Accordingly, the user may use this feedback to increase or decrease contact of the catheter with the moving heart wall to achieve the desired contact.

Before continuing, it is noted that any suitable analog and/or digital device may be implemented for indicating electrode-tissue contact to a user. In another exemplary embodiment, the electrical signals generated by piezoelectric sensor 20 may be further characterized using a suitable processing device such as, but not limited to, a desktop or laptop computer. Such processing device may be implemented to receive the voltage or charge signal generated by the piezoelectric sensor and convert it to a corresponding contact condition for the electrode 10 and output for the user e.g., at a display device.

It is also noted that the output device is not limited to a display device. For example, the electrode-tissue contact may be output to the user as an audio signal of tactile feedback (e.g., vibrations) on the handle of the catheter. In any event, circuitry for conveying output of the piezoelectric sensor to a user in one form or another may be readily provided by those having ordinary skill in the electronics arts after becoming familiar with the teachings herein.

Figure 5A:
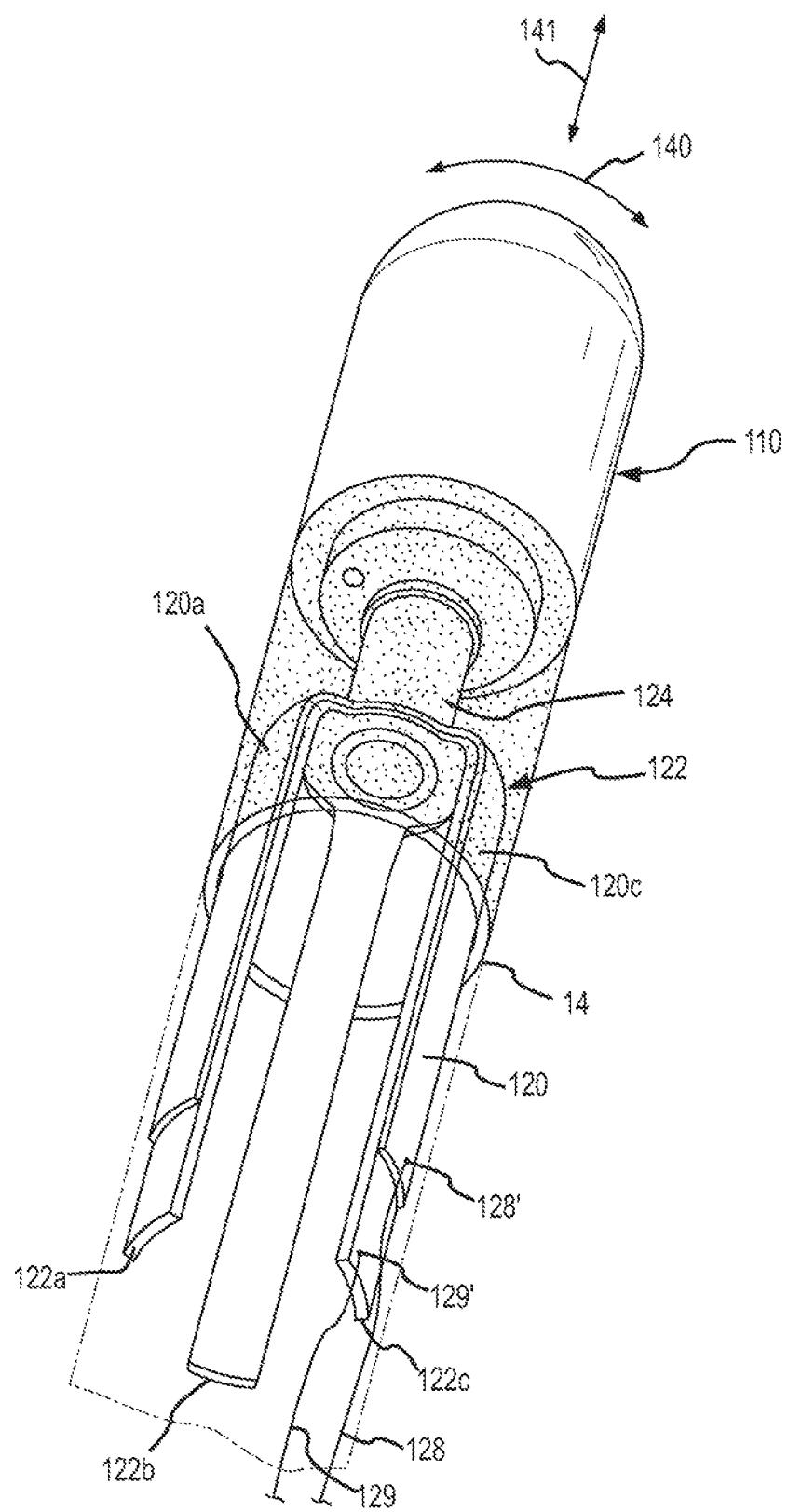
FIG. 5a-e are perspective views showing alternative embodiments for operatively associated at least one piezoelectric sensor with an electrode.
Figure 5B:
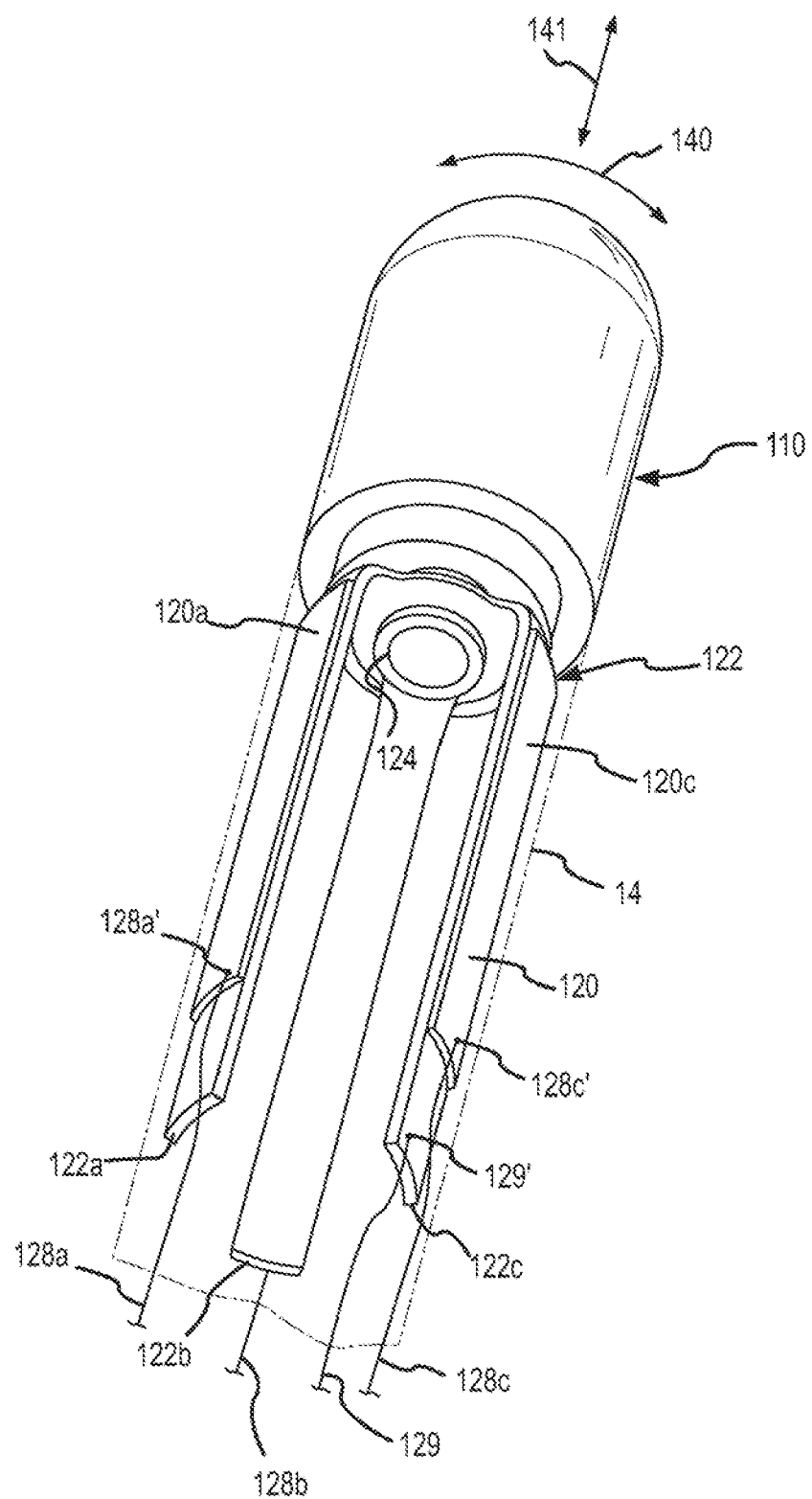
Figure 5C:
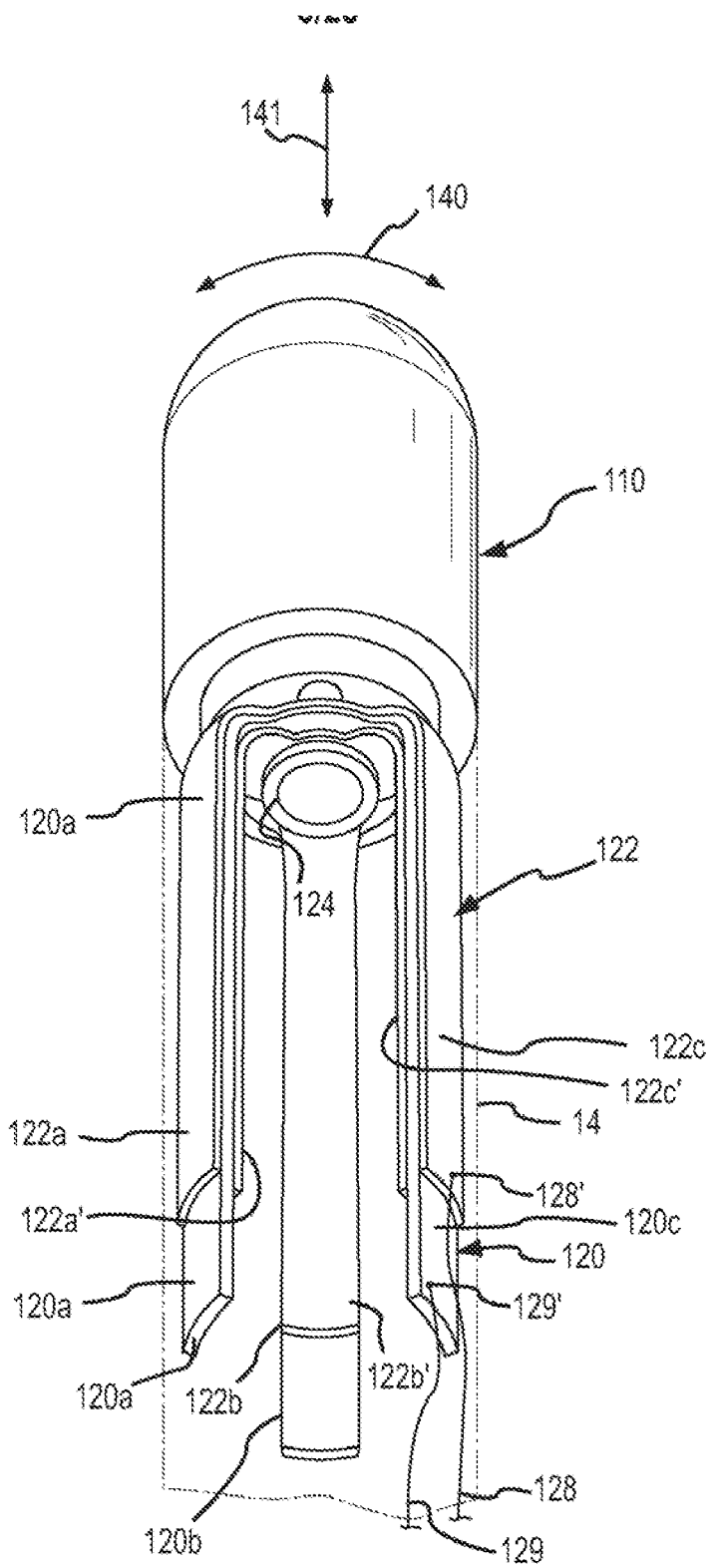

FIG. 5a-c are perspective views showing alternative embodiments for operatively associating at least one piezoelectric sensor 120 with an electrode 110. It is noted that 100-series reference numbers are used in the embodiments shown in FIG. 5a-c to refer to like elements described above with reference to FIGS. 2 and 2a. Therefore the description of some elements may not be repeated in the following discussion.

FIG. 5a is a perspective view showing a piezoelectric sensor 120 provided on supporting structure 122 which in turn is coupled to the electrode 110 with a shaft 124 in a spaced-apart relation relative to the electrode 110. Such an embodiment serves to provide thermal and electrical isolation of the piezoelectric sensors from the electrode. Furthermore the shaft 124 may be flexible. The flexibility of the coupling shaft may be used as a low pass mechanical filter to mitigate spurious high frequency signal artifacts.

It should also be noted that the shaft 124 may be solid or hollow. For example, the shaft 124 may be hollow to permit a fluid to flow through the shaft for use with irrigated catheters. Although not shown, a tube or other conduit may be connected to or pass through the shaft 124 and extend through the catheter shaft 114 to the handle portion (not shown).

FIG. 5b is a perspective view showing a plurality of separate piezoelectric sensors 120a-c (although only sensors 120a and 120b are visible). In this embodiment, the separate piezoelectric sensors 120a-c are mounted at least partially down each leg 122a-c of the supporting structure 122, but the separate piezoelectric sensors 120a-c are not electrically connected to one another. The supporting structure 122 may be mounted on neck portion 124 close to the electrode 110 as shown in FIG. 5b. Alternatively, the supporting structure 122 may be coupled to the electrode 110 with a 124 in a spaced-apart relation such as described above with reference to FIG. 5a.

it is noted that this embodiment requires additional wiring be provided through the catheter shaft 114 (or use of the wireless connection mentioned above). That is, electrical wiring 128a-c may be connected to each piezoelectric sensor 120a-c (e.g., as illustrated by connections 128a'-128c') and electrical wiring 129 may be connected to a common ground (e.g., as illustrated by connection 129' on leg 122c of the supporting structure 122 where the supporting structure 122 is an electrical conductor).

In use, the piezoelectric sensor 120 responds to mechanical stresses by generating electrical energy (e.g., a voltage or charge). In addition to detecting contact of the electrode with the target tissue the relative magnitude and direction of the signal obtained from each of the separate piezoelectric sensors 129a-c may be used to determine the direction and plane of contact of the electrode 110. The resulting electrical signal may be processed and/or otherwise output for the user so that the user is able to determine when the electrode 110 is positioned with the desired level of contact with the target tissue 12.

FIG. 5c is a perspective view showing a single-piece piezoelectric sensor 120 with arm portions 120a-c sandwiched between protective layers of the tripod legs. That is, arm portion 120a of the piezoelectric sensor 120 is sandwiched between protective layers 122a and 122a', portion 120b of the piezoelectric sensor 120 is sandwiched between protective layers 122b and 122b', and portion 120c of the piezoelectric sensor 120 is sandwiched between protective layers 122c and 122c'. Such a embodiment serves to provide additional mechanical support for the piezoelectric sensor 120, thereby increasing the stiffness of the sensing system and augmenting the output signal.

It is noted that the piezoelectric sensor 120 may be formed as a single piece, as shown in FIG. 5c, or separate piezoelectric sensors may be provided (e.g., as described above with reference to FIG. 5b). It is also noted that the supporting structure 122 may be mounted on neck portion 124 close to the electrode 110, as shown in FIG. 5c, or the supporting structure 122 may be coupled to the electrode 110 with a shaft 124 in a spaced-apart relation relative to the electrode 10 (e.g. as described above with reference to FIG. 5a).

Figure 5D:
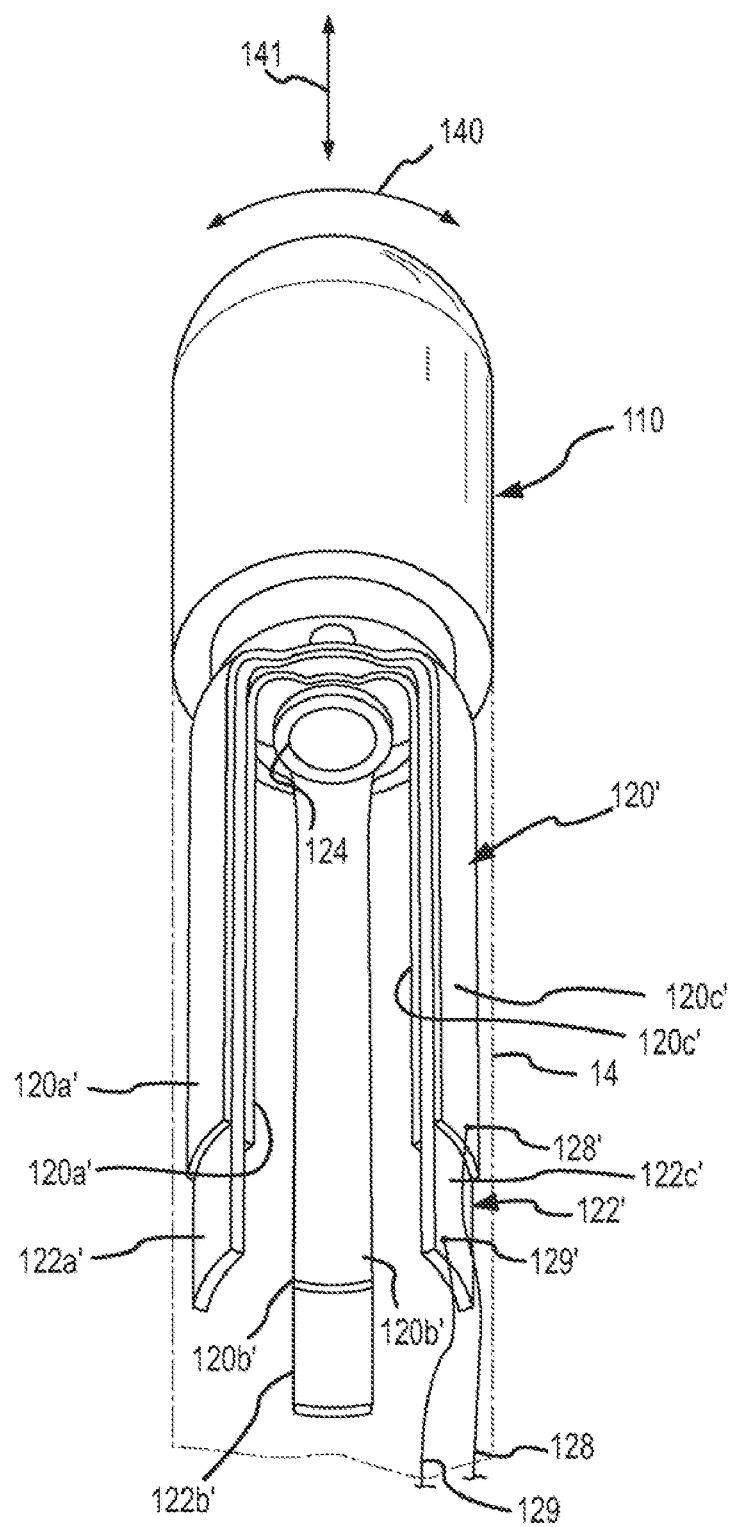

FIG. 5d is a perspective view showing the supporting structure (indicated by reference 122') sandwiched between two single-piece piezoelectric sensors 120a' (and 120b' and 120c' for each leg). The signals from the two piezoelectric sensors may be combined to improve the sensitivity of the contact sensing. Additionally, because stress response of piezoelectric materials is anisotropic, the two layers may be oriented differently with respect to each other to either attenuate directional differences in sensitivity or provide directional information of electrode-tissue contact.

It is noted that the piezoelectric sensors 120a' (and 120b' and 120c' for each leg) may be formed as a single piece, as shown in FIG. 5d, or separate piezoelectric sensors may be provided (e.g., as described above with reference to FIG. 5b).

It is also noted that the supporting structure 122' may be mounted on neck portion 124 close to the electrode 110, as shown in FIG. 5c, or the supporting structure 122' may be coupled to the electrode 110 by shaft 124 in a spaced-apart relation relative to the electrode 110 (e.g., as described above with reference to FIG. 5a).

Figure 5E:
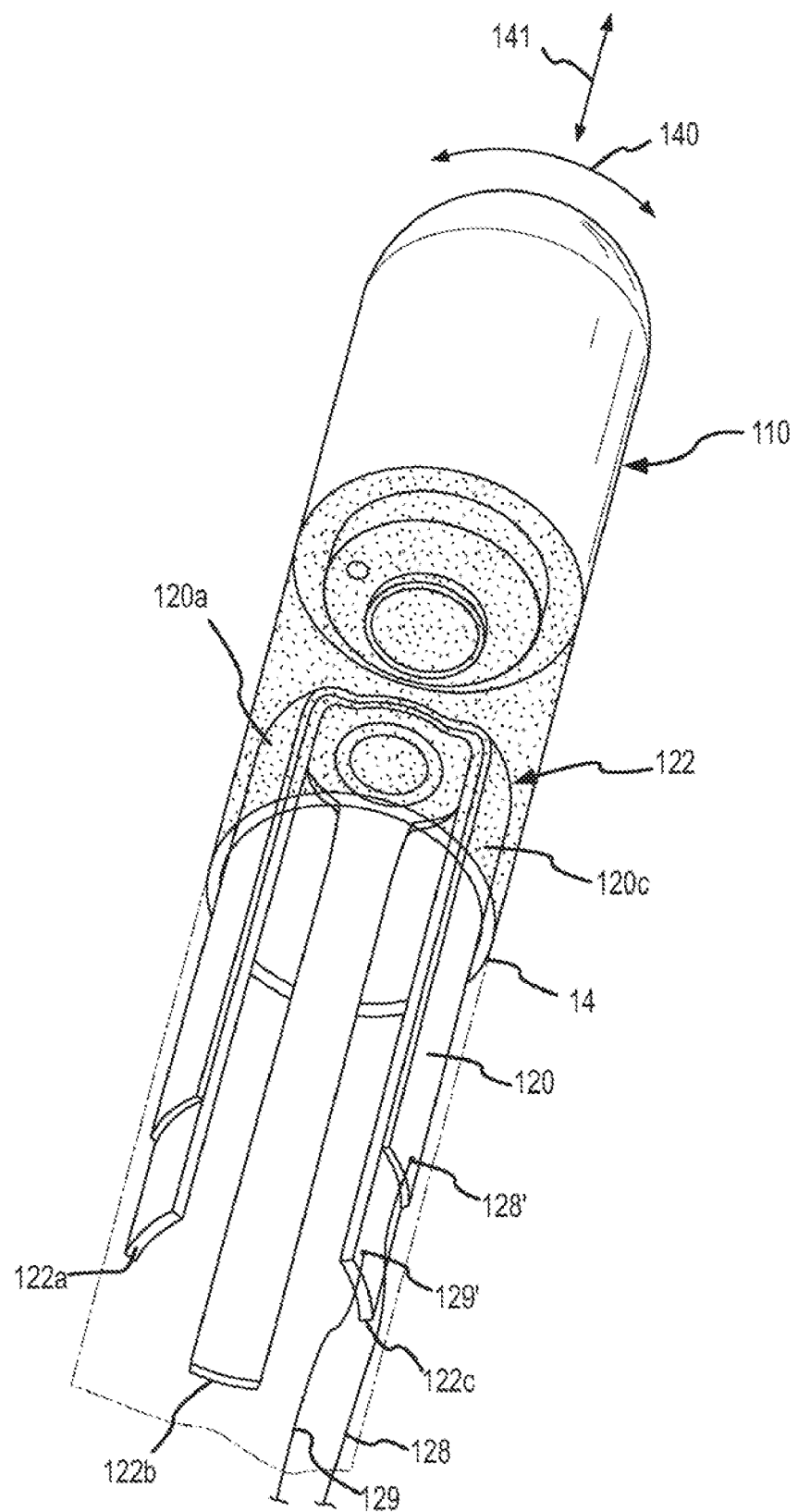

FIG. 5e is a perspective view showing a piezoelectric sensor 120 provided on supporting structure 122 in a spaced-apart relation to the electrode 10 (as shown in FIG. 5a, but not connected to the shaft 124). Such an embodiment serves to provide thermal and electrical isolation of the piezoelectric sensors from the electrode. Instead, the piezoelectric sensor 12 may be mounted within the catheter shaft (e.g., within a compliant material). The compliant material may act as a mechanical coupler as well as a low pass mechanical filter to mitigate spurious high frequency signal artifacts.

Figure 6A:
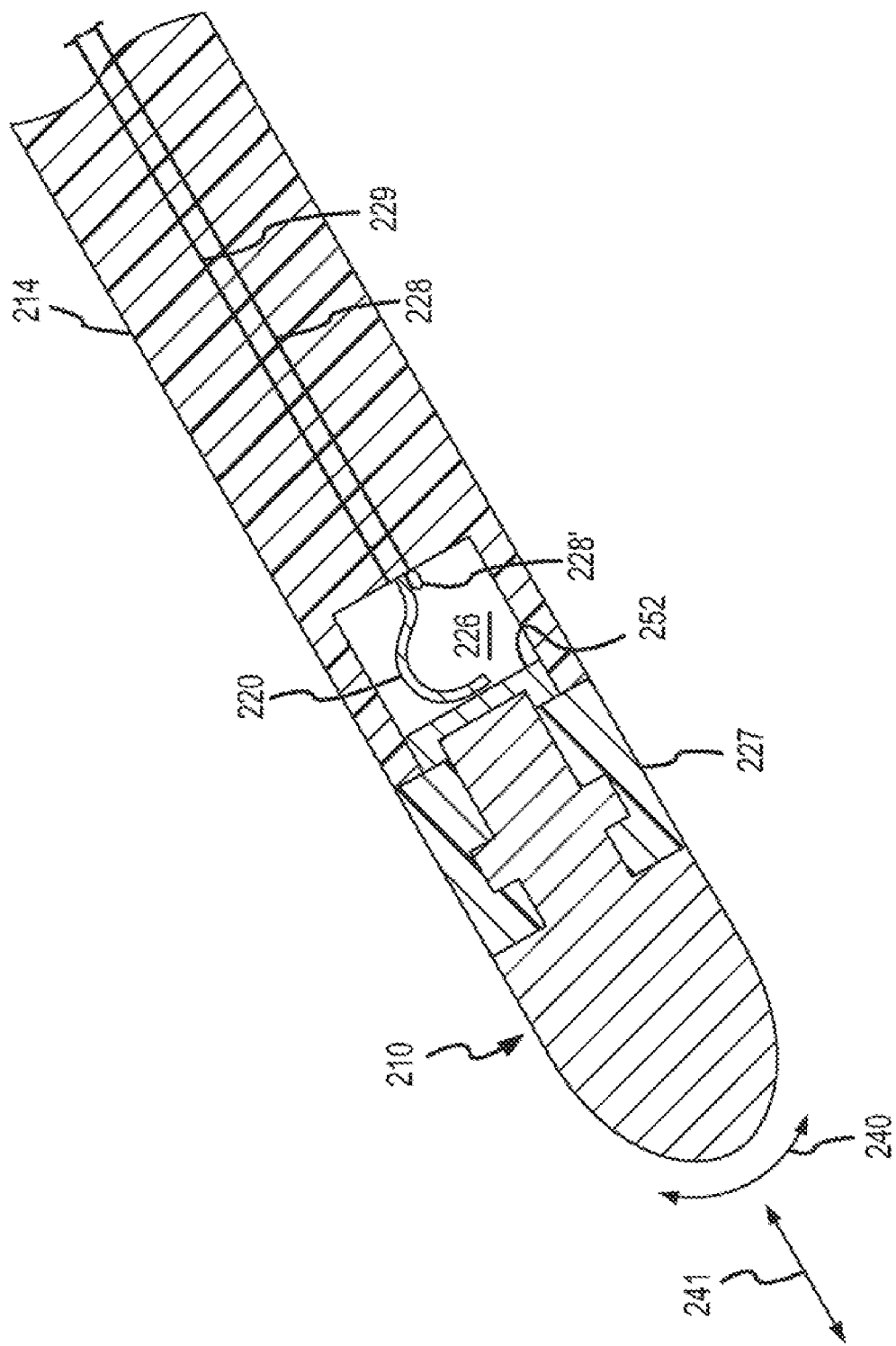
FIG. 6a-c are cross-sectional views showing more alternative embodiments for operatively associating at least one piezoelectric sensor with an electrode.
Figure 6B:
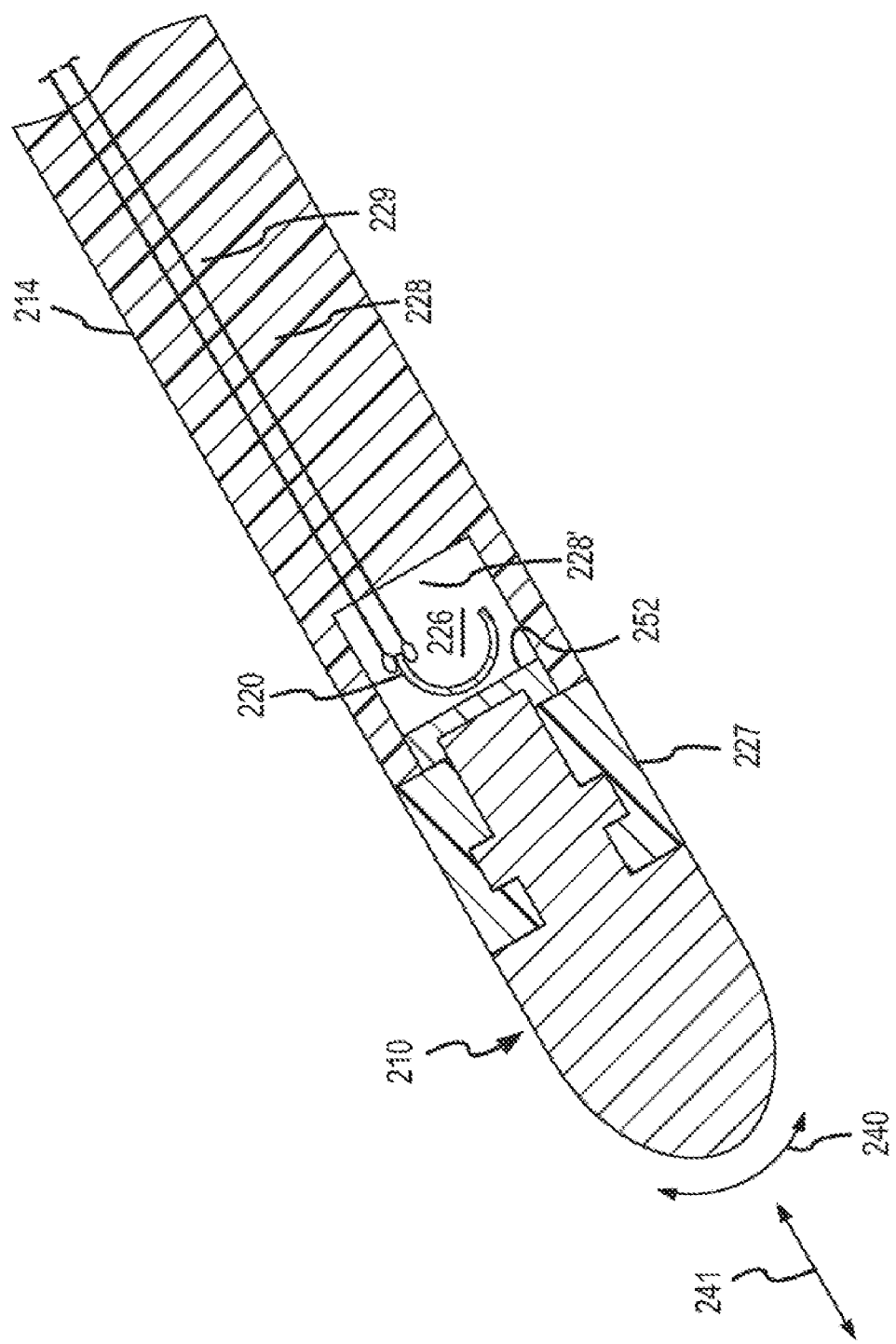
Figure 6C:
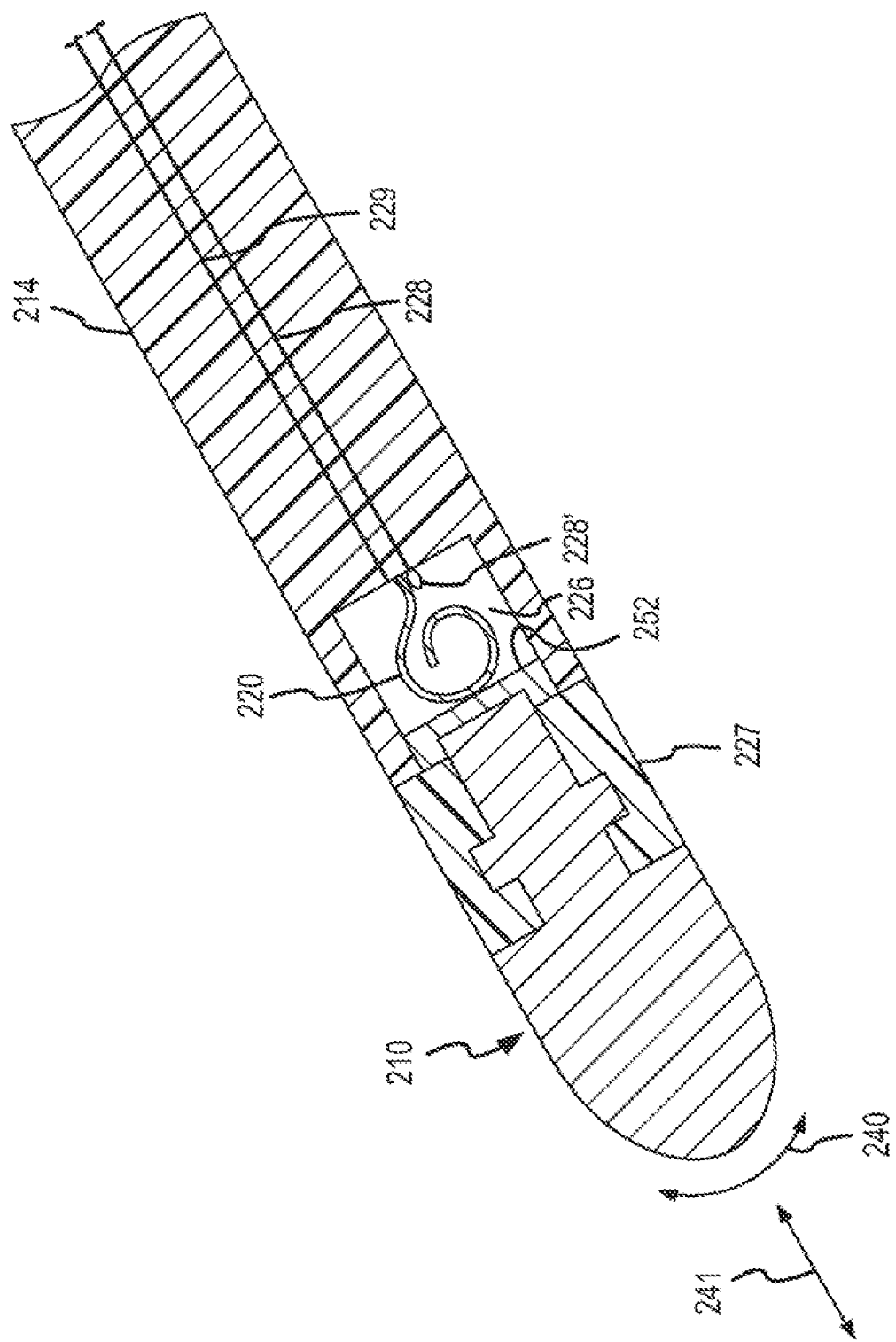

FIG. 6a-c are cross-sectional views showing still more alternative embodiments for operatively associating at least one piezoelectric sensor 220 with an electrode 210. It is noted that 200-series reference numbers are used in the embodiments shown in FIG. 6a-c to refer to like elements described above with reference to FIGS. 2 and 2a. Therefore the description of some elements may not be repeated in the following discussion.

In each of these embodiments the piezoelectric sensor 220 is provided near or adjacent the electrode 210, but is not connected directly to the electrode 210. Such an embodiment serves to electrically as well as thermally, isolate the piezoelectric sensor 220 from the electrode 210, while still enabling the piezoelectric sensor 220 to respond to stress on the electrode 210 during use (e.g., in the direction of arrows 240 and/or 241).

In one example, the piezoelectric sensor 220 is provided directly adjacent an optional insulating material 252, which in turn is in direct contact with the electrode 210. The piezoelectric sensor 220 may be provided in a compliant material 226, such as silicone, or airspace. Contact of the electrode 210 with the target tissue causes a stress or strain on the piezoelectric sensor 220, which in turn responds to stresses on the electrode 210 (e.g., in the directions illustrated by arrows 240 and/or 241) by generating electrical (voltage or charge) signals. These electrical signals may be viewed by the user, e.g., as output on an electrical monitoring device.

In FIG. 6a, the piezoelectric sensor 220 is substantially a "question mark" shape. In FIG. 6b, the piezoelectric sensor 220 is substantially an arc or half-circle shape. In FIG. 6c, the piezoelectric sensor 220 is substantially a spiral shape. Of course other shapes for the piezoelectric sensor 220 are also contemplated, as will be readily apparent to those having ordinary skill in the art after becoming familiar with the teachings herein. It is noted that the piezoelectric sensor 220 may be a stand-alone laminated structure (e.g., as shown in FIG. 3a-c) and/or may be provided on a flexible support structure (e.g., a metal "frame" or silicone).

Although not shown in FIG. 6a-c, the flexible support structure may be shaped substantially the same as the piezoelectric sensor 220 shown in FIG. 6a-c. Also not shown in FIG. 6a-c, it is noted, however, that the electrode 210 may be spring-biased using a spring or other suitable elastic material to bias the electrode 210 in a forward position.

Figure 7A:
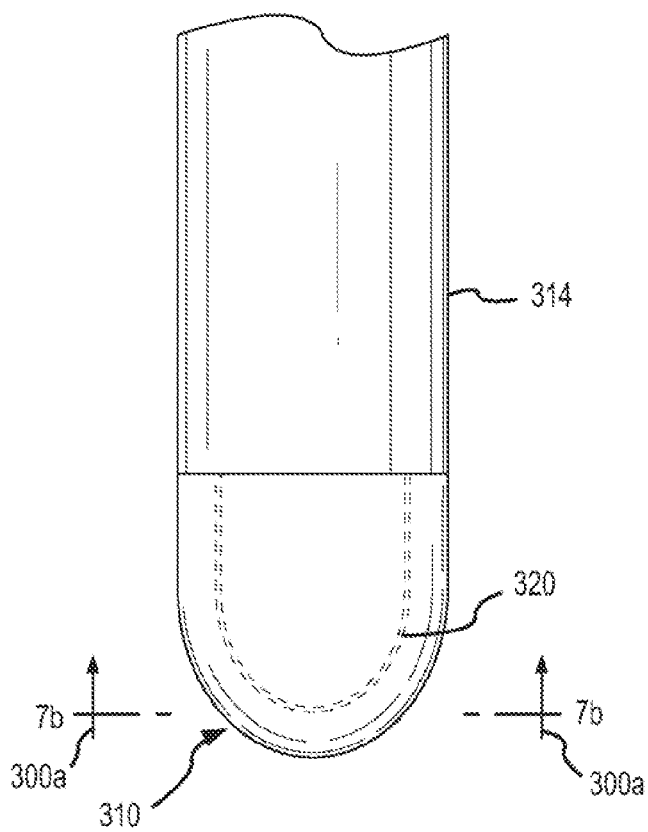
FIG. 7a-g are perspective views and corresponding cross-sectional views showing more alternative embodiments for operatively associating at least one piezoelectric sensor with an electrode.
Figure 7B:
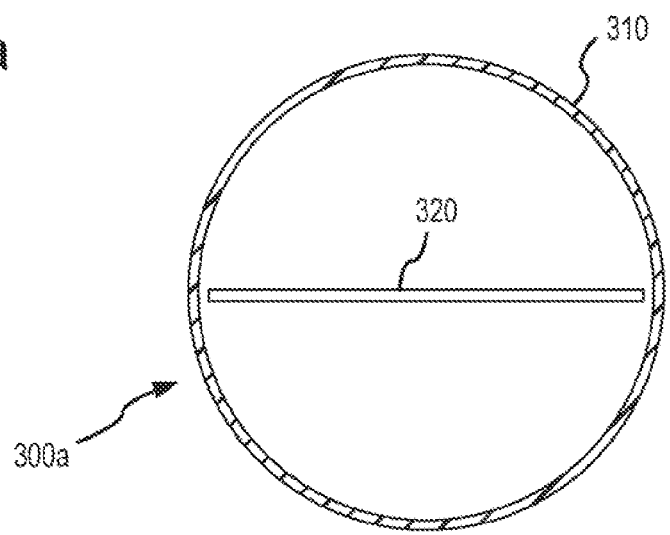

FIG. 7a-g are perspective views showing still more alternative embodiments for operatively associating at least one piezoelectric sensor 320 with an electrode 310. Cross-sectional views are also shown in FIGS. 7b, d, and f so that the arrangement of the piezoelectric sensor(s) can be better seen within the electrode 310. It is noted that 300-series reference numbers are used in the embodiments shown in FIG. 7a-g to refer to like elements described above with reference to FIGS. 2 and 2a. Therefore the description of some elements may not be repeated in the following discussion.

Figure 7C:
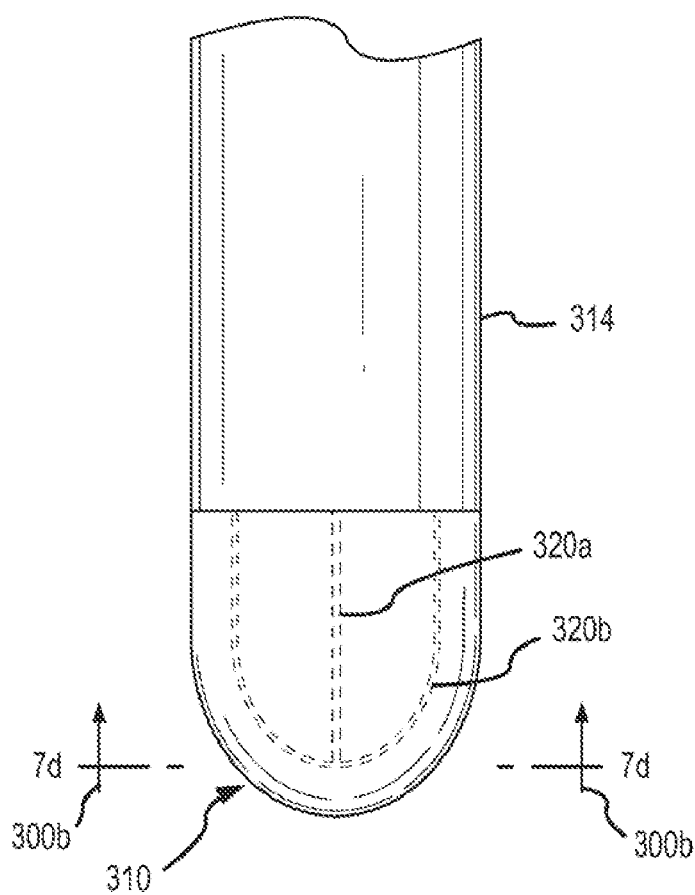
Figure 7D:
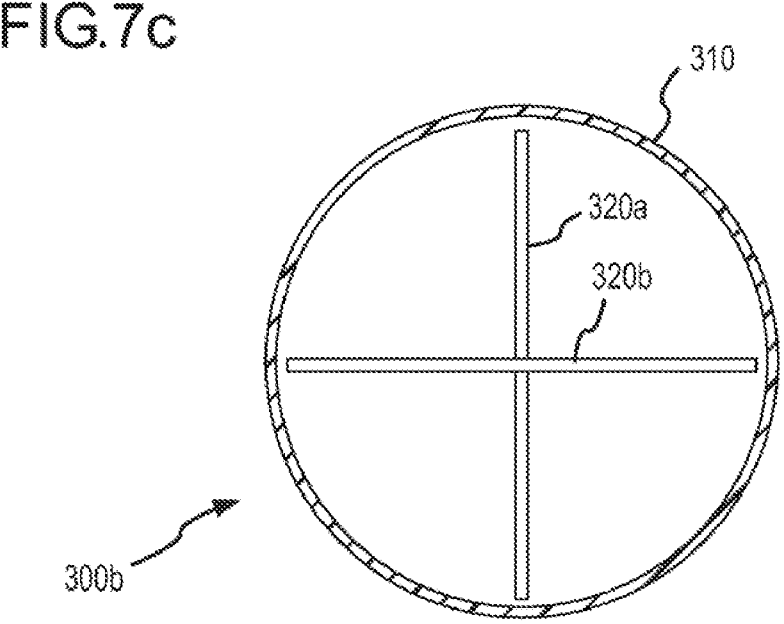
Figure 7E:
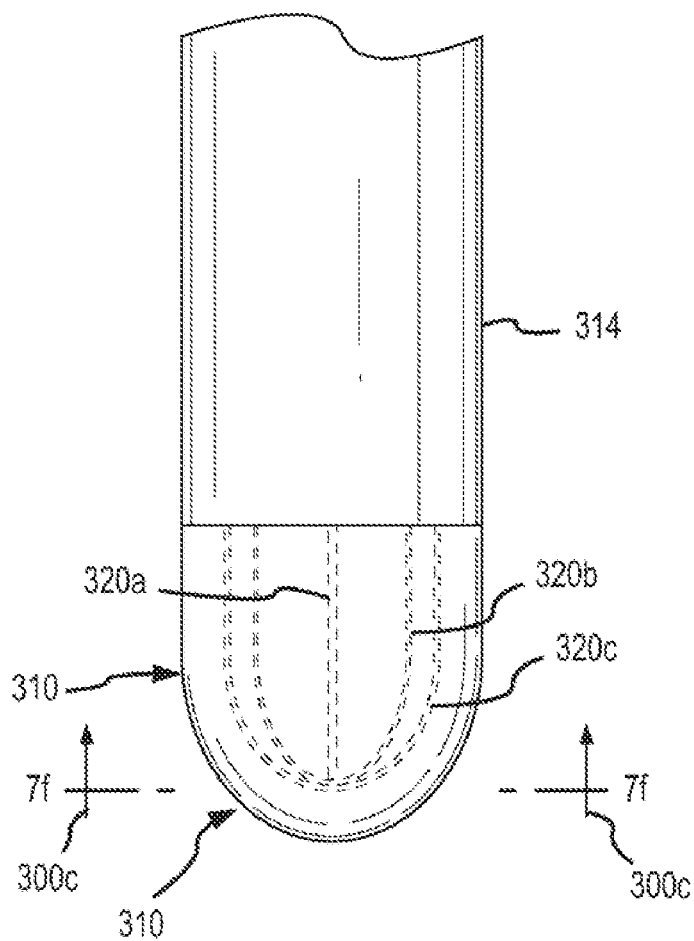
Figure 7F:
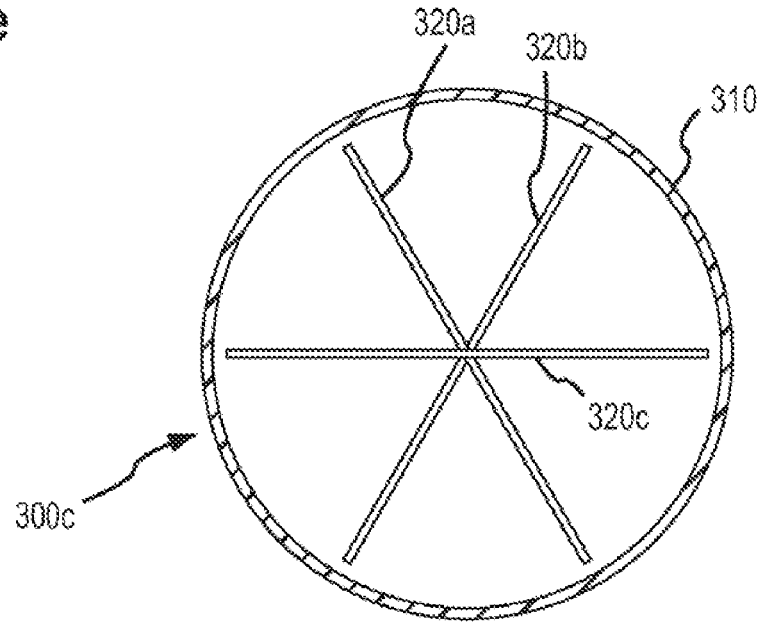

In FIG. 7a, an arcuate piezoelectric sensor 320 is housed in the electrode 310. It is noted that the piezoelectric sensor 320 may be integrally molded within the electrode 310 and/or anchored within the catheter shaft 314. In FIG. 7b, cross-sectional view 300a is taken along lines 7b-7b in FIG. 7a and shows the arrangement of the piezoelectric sensor 320 in the electrode 311. In FIG. 7c, two arcuate piezoelectric sensors 320 are housed in the electrode 310. The piezoelectric sensors 320 may be mounted substantially perpendicular to one another, as better seen in the FIG. 7d, the cross-sectional view taken along lines 7d-7d in FIG. 7c. In FIG. 7e, three arcuate piezoelectric sensors 320 are housed in the electrode 310. The piezoelectric sensors 320 can be mounted from 30-180 degrees radial offset for example sixty degrees, relative to one another, as better seen in the cross-sectional view of FIG. 7f taken along lines 7f-7f in FIG. 7e.

Figure 7G:
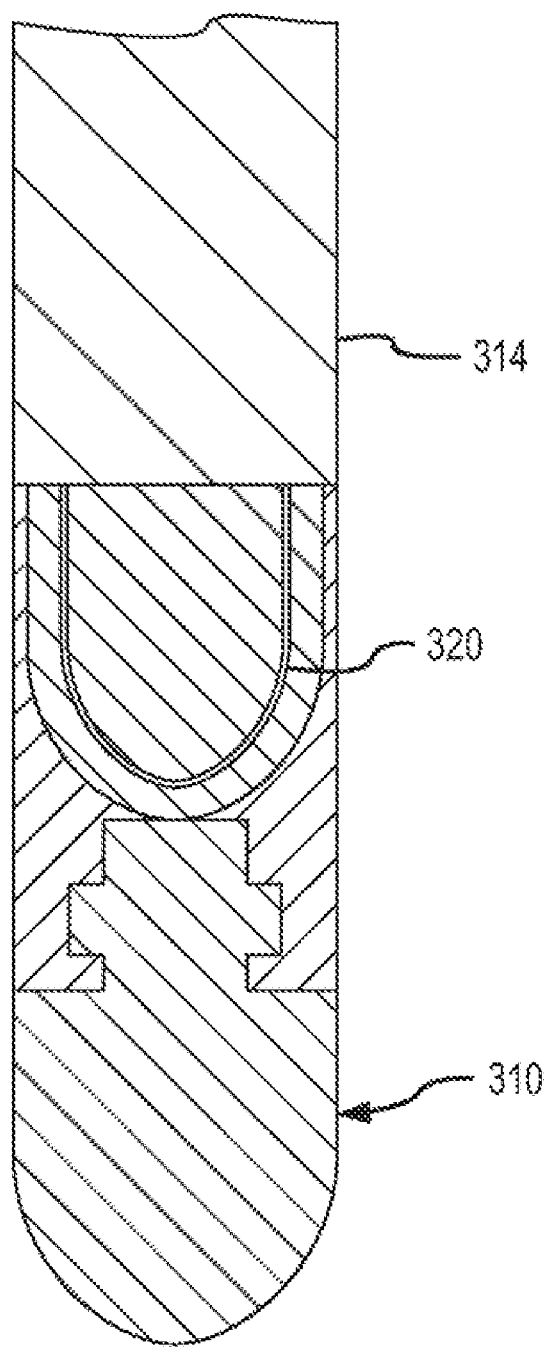

In FIG. 7g, an arcuate piezoelectric sensor 320 is mounted behind the electrode 310 (e.g., similarly to the embodiments described above for FIG. 6a-c). Of course the piezoelectric sensor 320 is not limited to the single arcuate sensor shown in FIG. 7g. Other embodiments, such as those shown in FIG. 7c and 7e may also be implemented.

It is noted that the configurations shown in FIG. 7a-7f (where the piezoelectric sensors 320 are housed within the electrode 310) enable manufacturing of relatively small sizes ad therefore are particularly suitable for use, e.g., in so-called brush electrodes. However, these embodiments are not limited to any particular size or use. It is also noted that other shapes and arrangements of the piezoelectric sensor(s) 320 are also contemplated for the embodiments shown in FIG. 7a-g, as will be readily apparent to those having ordinary skill in the art after becoming familiar with the teachings herein.

FIG. 8a-8h are cross-sectional views showing more alternative embodiments for operatively associating at least one piezoelectric sensor with an electrode, and corresponding cross-sectional views showing exemplary response of the piezoelectric sensor to stress of the electrode. It is noted that 400-series reference numbers are used in the embodiments shown in FIG. 8a-h to refer to like elements described above with reference to FIGS. 2 and 2a. Therefore the description of some elements may not be repeated in the following discussion.

In FIG. 8a-f, the piezoelectric sensor 420 is operatively associated with the electrode 410 via a translation element 450 positioned between the electrode 410 and the piezoelectric sensor 420. Optionally, the piezoelectric sensor 420 may be electrically and thermally isolated from the electrode 410, such as by using an insulating material 452 between the electrode 410 and the translation element 450 as shown in FIGS. 8a-d and 8g-h but not in FIG. 8e-f).

Also optionally, a backing element 451 may be provided adjacent the piezoelectric sensor 420 on a side opposite (or "behind") the translation element 450. Backing element 451 provides mechanical Support for the piezoelectric sensor 420 and holds the piezoelectric sensor 420 against the translation element 450, without restricting operation of the piezoelectric sensor 420. Furthermore, the backing element 451 provides stress and response modification such as low pass mechanical for the piezoelectric sensor 420.

Figure 8A:
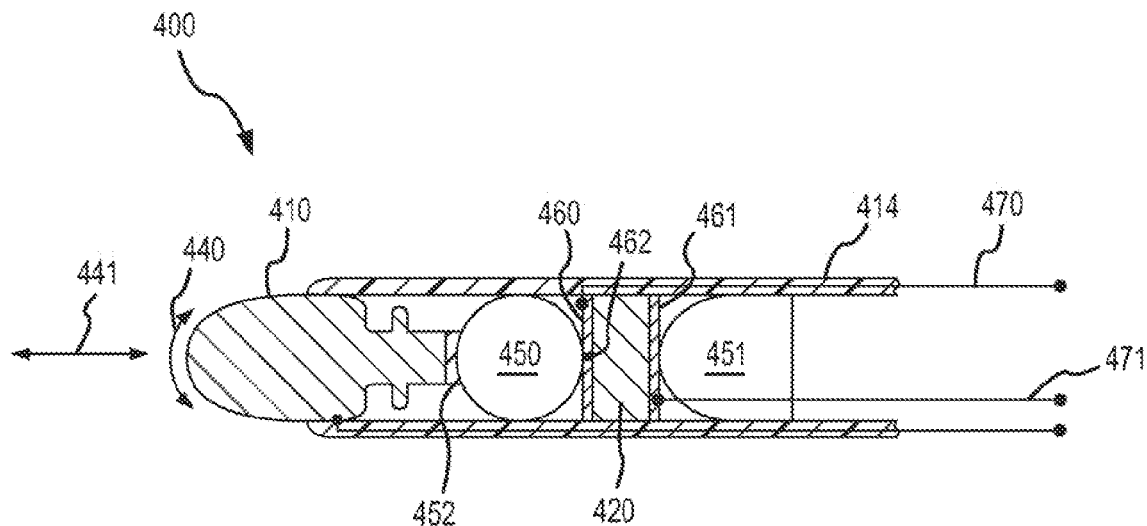
FIG. 8a-h are cross-sectional views showing more alternative embodiments for operatively associating at least one piezoelectric sensor with an electrode, and corresponding cross-sectional views showing exemplary response of the piezoelectric sensor to stress of the electrode.
Figure 8B:
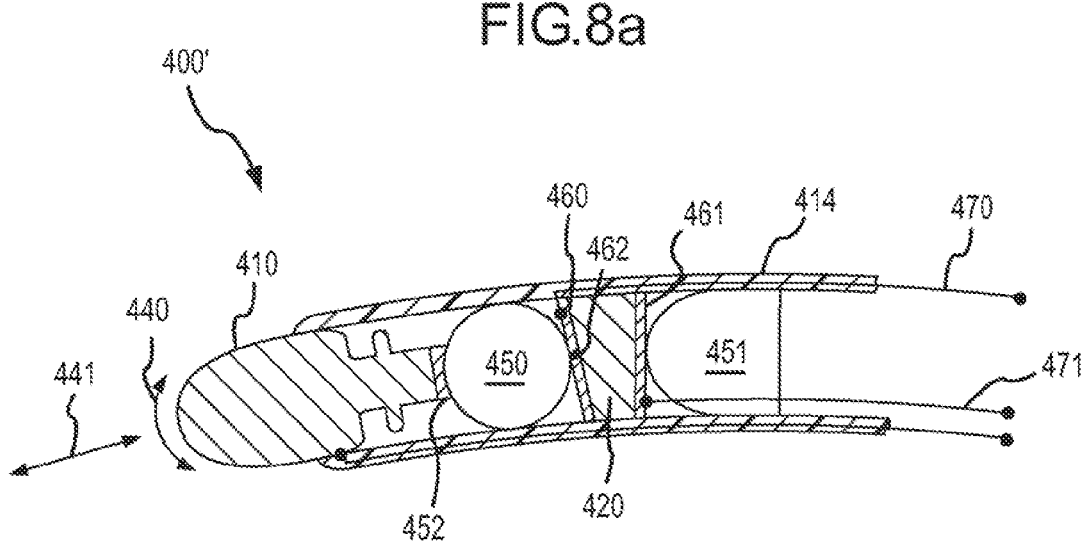
Figure 8C:
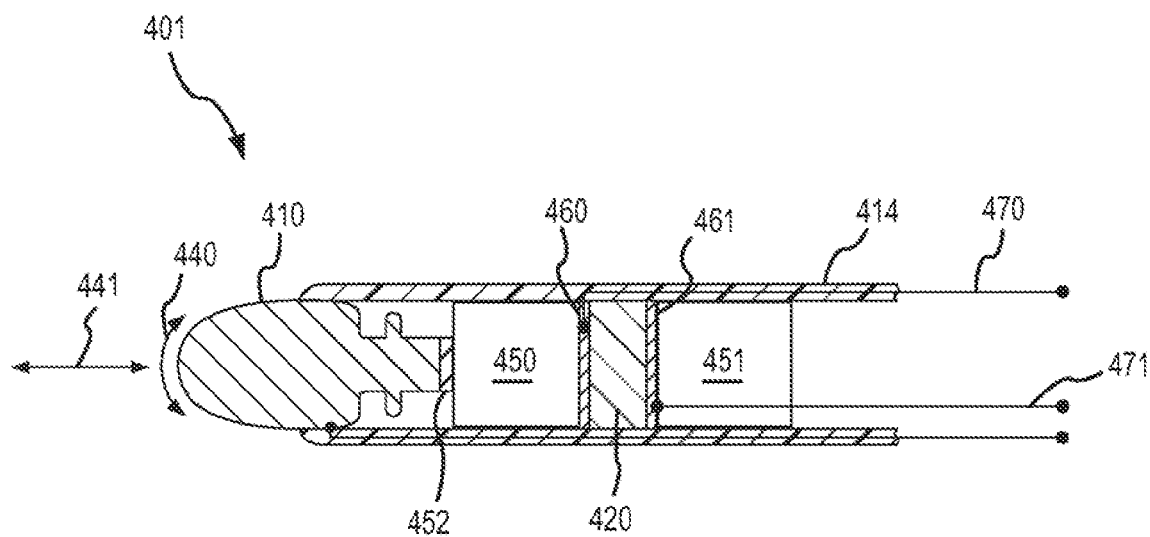
Figure 8D:
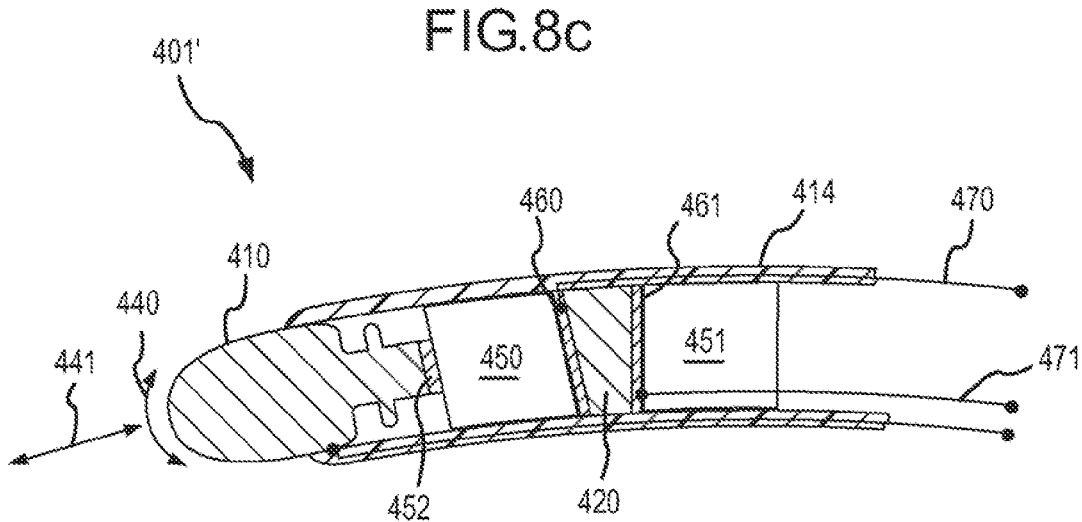
Figure 8E:
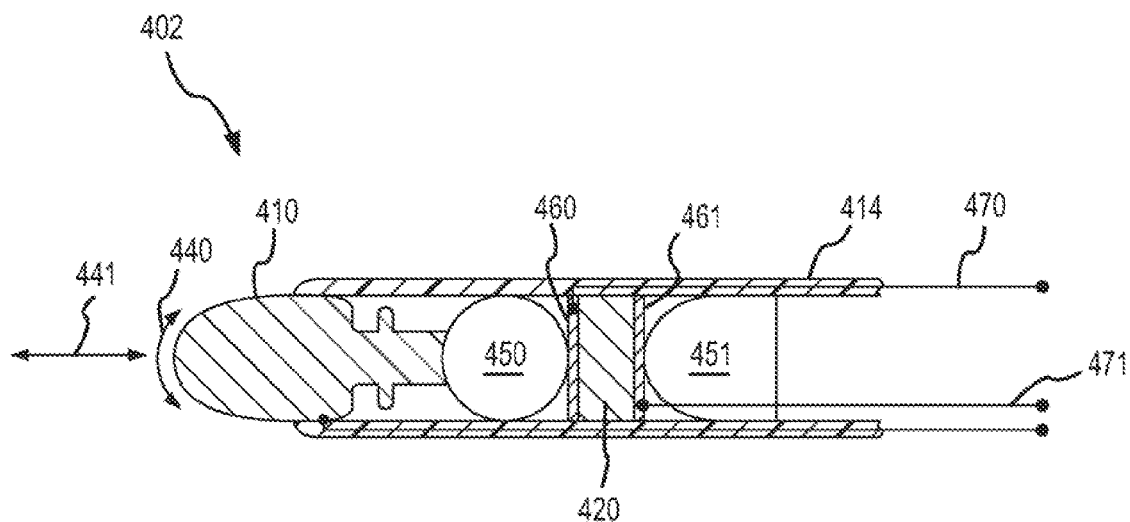
Figure 8F:
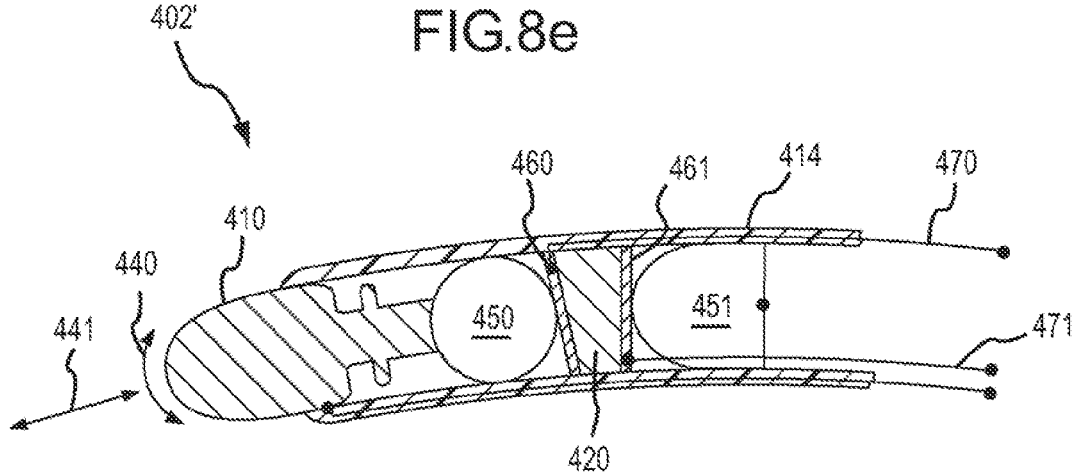
Figure 8G:
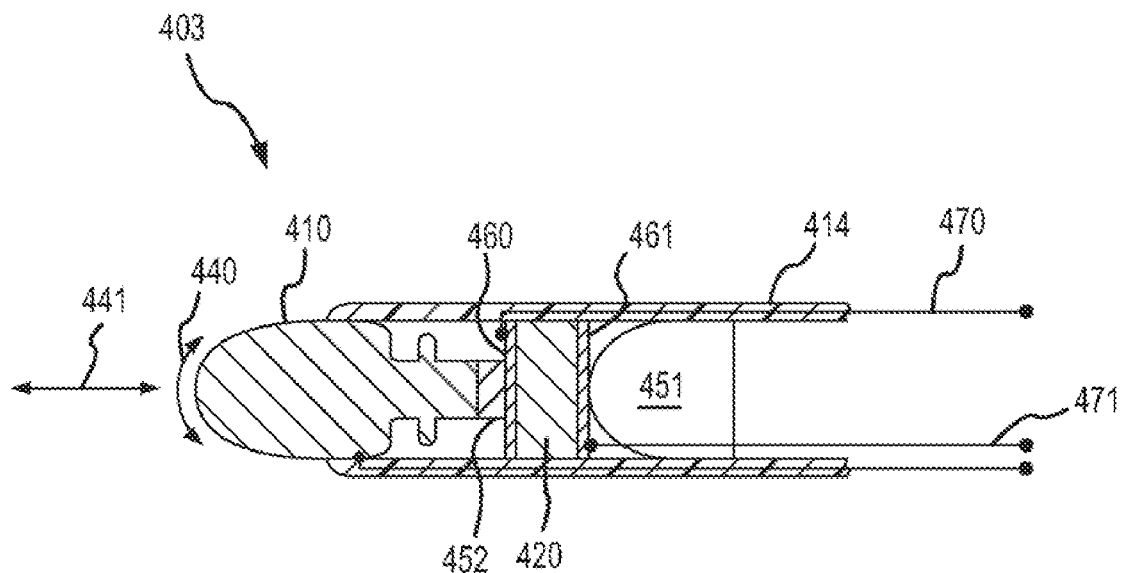
Figure 8H:
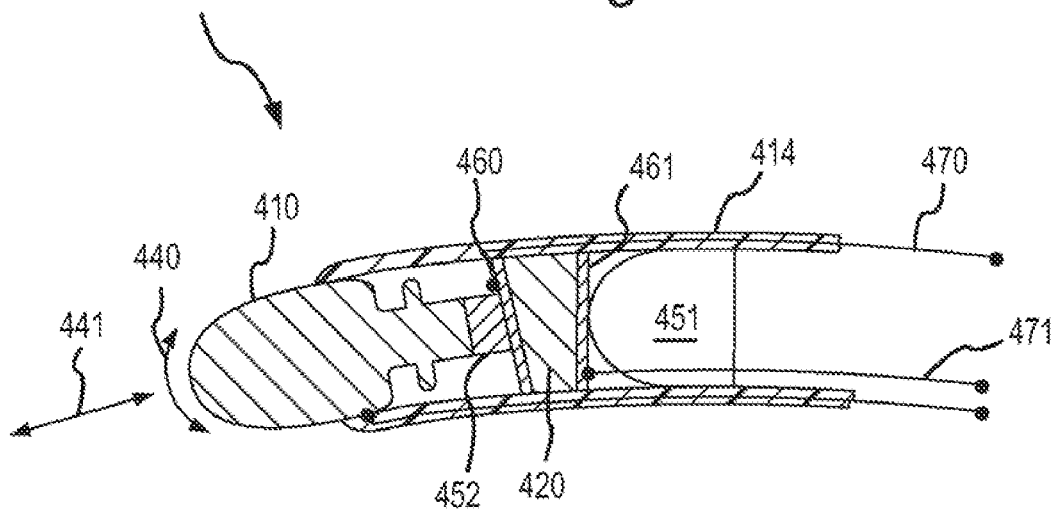

The translation element 450 may be manufactured of any suitable elastic material, such as, e.g., stainless steel. The translation element 450 may also be any suitable shape. In FIG. 8a-b, the translation element 450 is shown as being substantially spherical-shaped. In FIG. 8c-d, the translation element 450 is shown as being substantially square-shaped. Other shapes are also contemplated, such as, e.g., elliptical, rectangular triangular etc.

The support element 451 may also be manufactured of any suitable elastic material (e.g., the same stainless steel that the translation element 450 is manufactured from). The elastic material allows the elements 450 and 451 to absorb pressure that may be applied head-on to the electrode 410 without damaging the piezoelectric sensor 420. The support element 451 may also be any suitable shape, e.g., as discussed above for the translation element 450.

It is noted that translation element 450 and support element 451 are not limited to any particular shape or manufacture of any particular material. The material these elements 450 and 451 are manufactured from, and the shape of these elements 450 and 451, may be selected based on various design considerations (e.g., desired sensitivity, durability, etc.) to enable the piezoelectric sensor 420 to respond to stress or flexure of the electrode 410.

Stress of the electrode 410 due to contact with the tissue is transmitted to the piezoelectric sensor 420 via the translation element 450. This operation may be better understood with reference to the neutral states 400 to 403 and corresponding flexed states 400' to 403' shown respectively in FIG. 8*a-h*. It can be seen that when the electrode 410 moves in the direction of arrow 440 (and/or pressure/strain being applied head on to electrode 410 in the direction of arrows 441), movement of the electrode 410 causes the translation element 450 to move (although very slightly) along the outside edge of the piezoelectric sensor 420. As the translation element 450 moves it compresses the lower portion and stretches the upper portion of the piezoelectric sensor 420 ("upper" and "lower" referring to the view in FIG. 8*a-h*). Of course the compression and stretching is on the order of sub-millimeters and therefore is not actually as pronounced as it is shown in the exaggerated illustration of FIG. 8*a-h*.

It is noted that these stresses or strains on piezoelectric element 420 occur in the G33 plane, as described in more detail above with reference FIG. 3*c*. Again, the piezoelectric sensor 420 responds to movement or deflection of the electrode 410 (e.g., in the directions illustrated by arrows 440 and/or 441) by generating electrical (voltage or charge) signals which may be viewed by the user, e.g., as output on an electrical monitoring device.

Electrical wiring 470 may be connected to the piezoelectric sensor 420 at conductive layer 460. Electrical wiring 471 may also be connected to the piezoelectric sensor 420 at conductive layer 461, or to a ground (e.g., as illustrated by 451 of the supporting structure where the supporting structure 451 is an electrical conductor). It is noted that only one wire needs to be connected to the piezoelectric sensor 420 (and one wire to ground) in this embodiment if the piezoelectric sensor 420 is formed as a single piece. The wires may extended through the catheter shaft to deliver electrical signals from the piezoelectric sensor 420 to a data acquisition/processing/output device (not shown), such as e.g., an echocardiogram (ECG) device. Alternatively, a wireless connection may be implemented, e.g., by providing a transmitter in the catheter and a receiver in association with the data acquisition/processing/output device.

FIG. 9*a-f* are side and corresponding cross-sectional views showing more alternative embodiments for operatively associating at least one piezoelectric sensor 520 with an electrode 510. The cross-sectional views are shown so that the arrangement of the piezoelectric sensor(s) can be better seen within the electrode 510. It is noted that 500-series reference numbers are used in the embodiments shown in FIG. 9*a-f* to refer to like elements described above with reference to FIGS. 2 and 2*a*. Therefore the description of some elements may not be repeated in the following discussion.

In each of these embodiments, the piezoelectric sensor 520 is provided on a support structure 522 (e.g., a pole) connected to the electrode 510. The piezoelectric sensor 520 may be provided in a compliant material 526, such as silicone or airspace. Contact of the electrode 510 with the target tissue causes the support structure to move and results in a stress or strain on the piezoelectric sensor 520, which in turn responds to stresses on the electrode 510 (e.g., in the directions illustrated by arrows 540 and/or 541) by generating electrical (voltage or charge) signals. These electrical signals may be viewed by the user, e.g., as output on an electrical monitoring device.

Figures 9A, 9B:
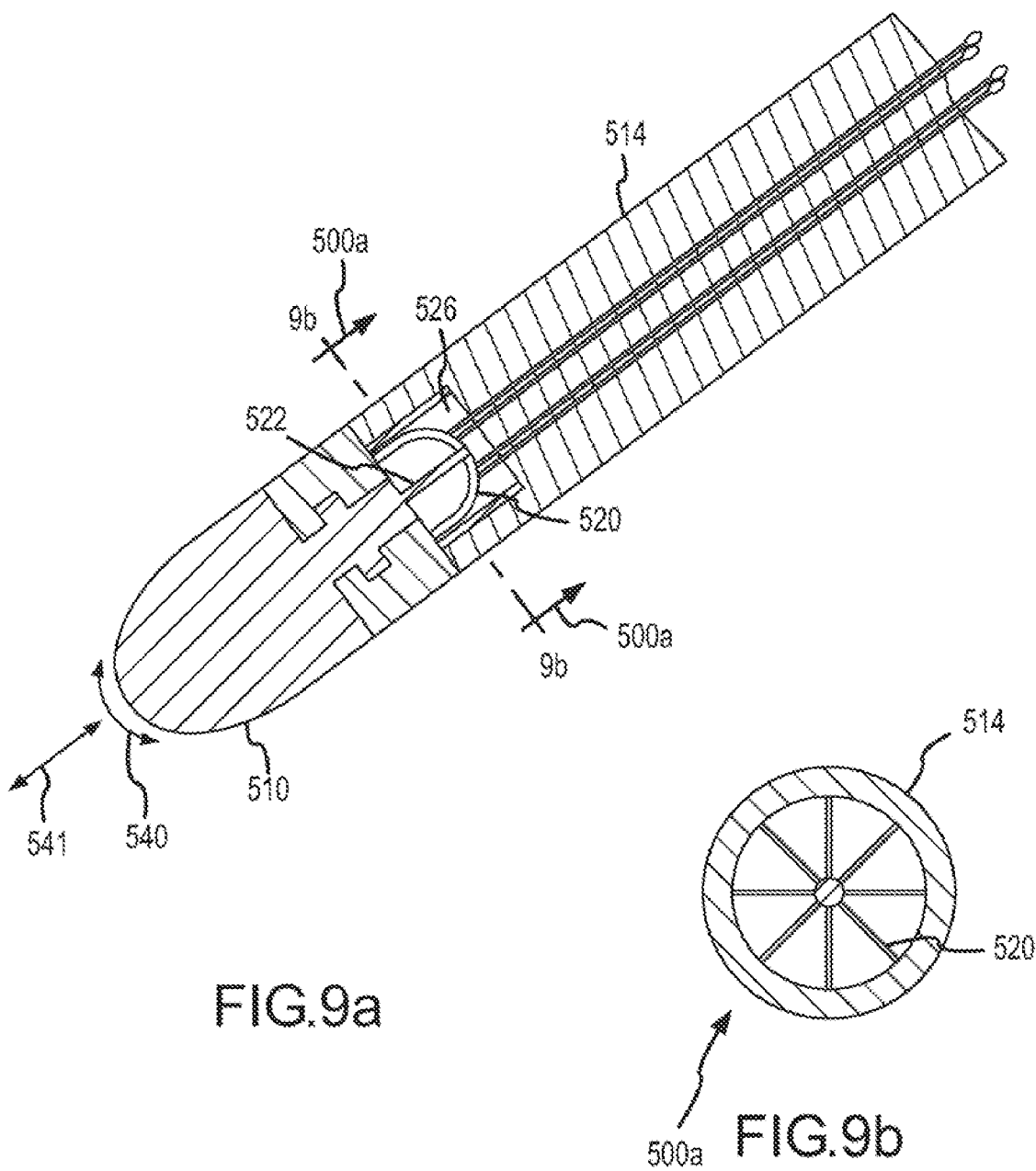
FIG. 9a-f are side and corresponding cross-sectional views showing more alternative embodiment for operatively associating at least one piezoelectric sensor with an electrode.
Figure 9C:
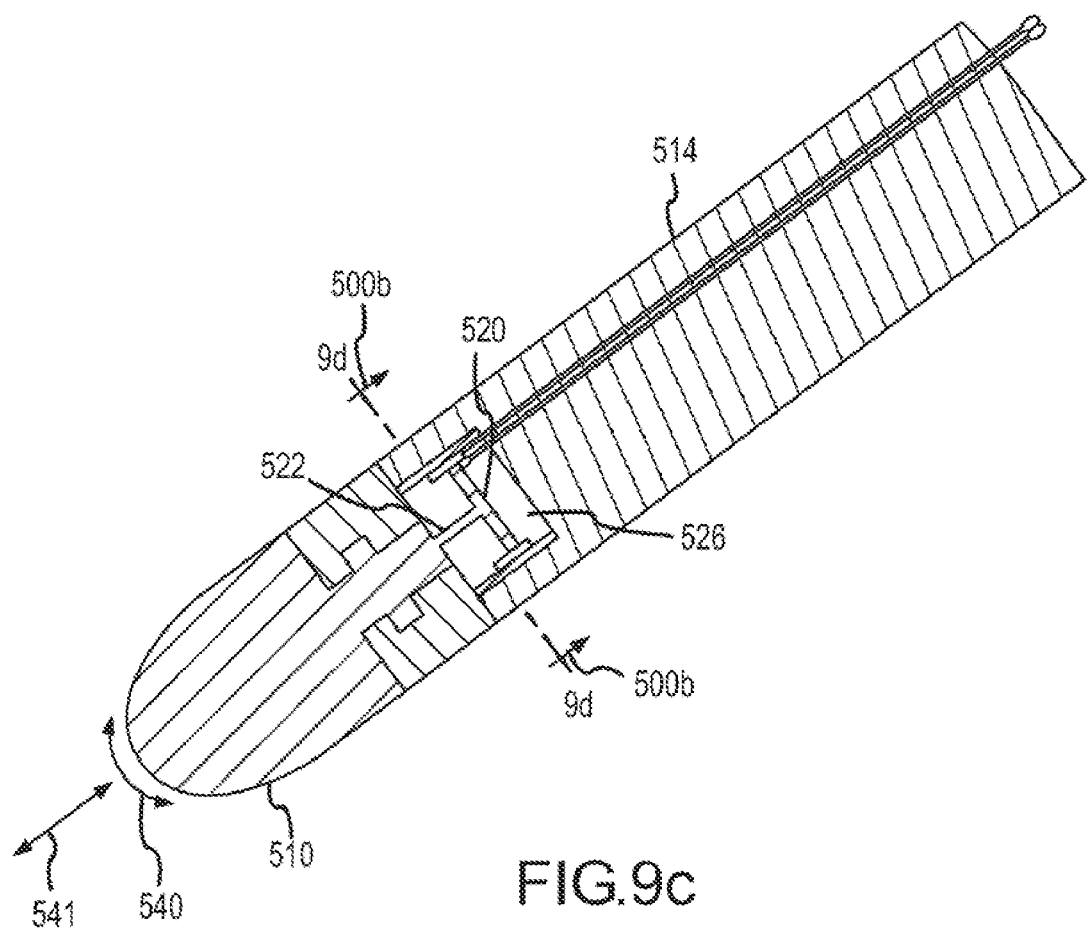
Figure 9D:
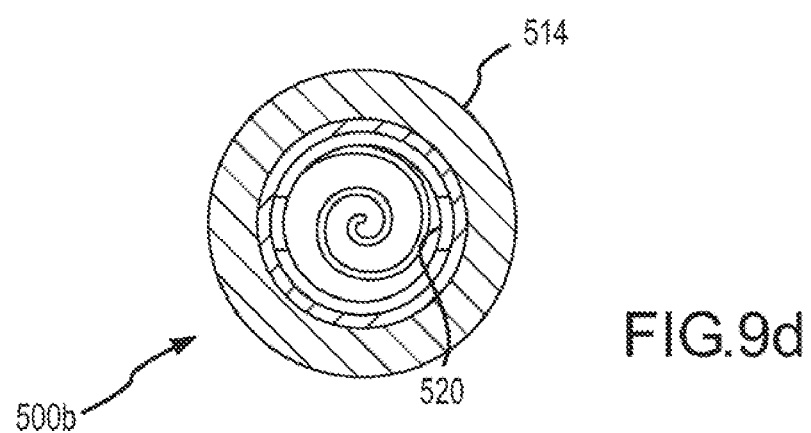
Figure 9E:
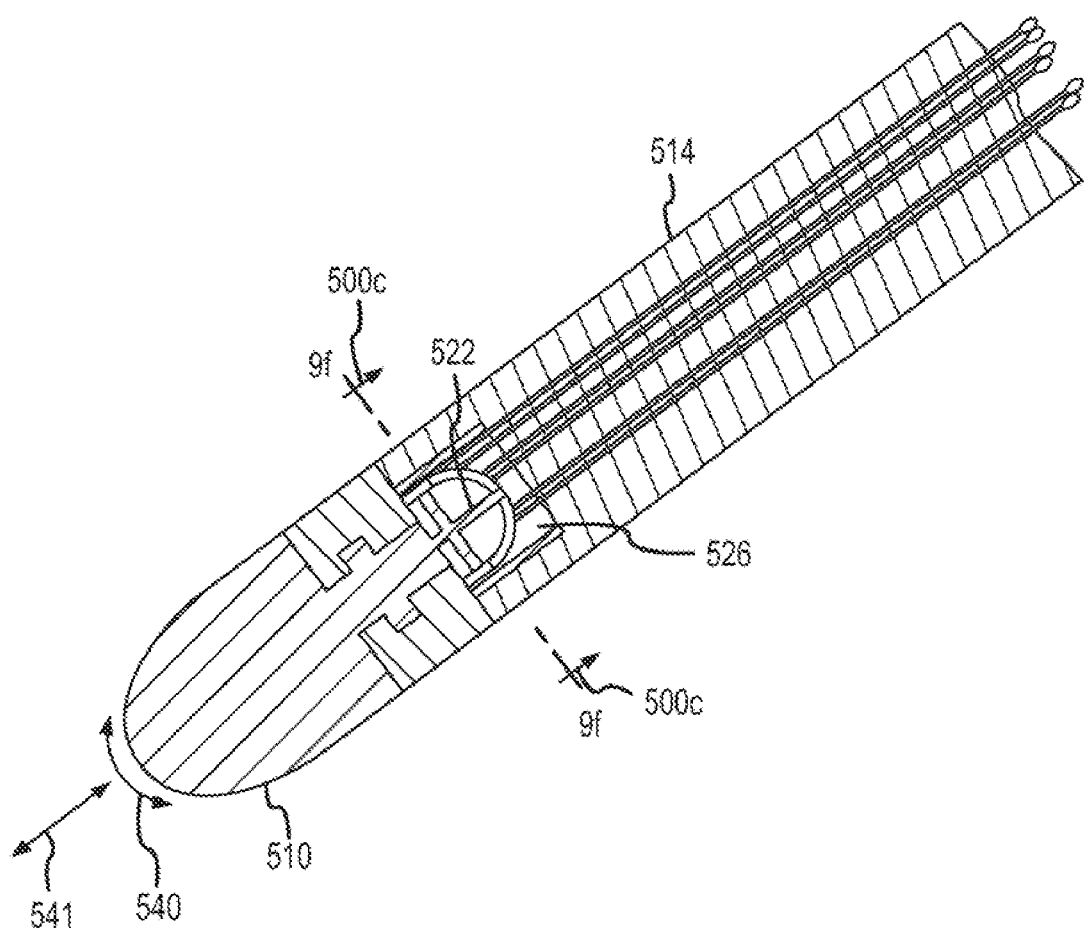
Figure 9F:
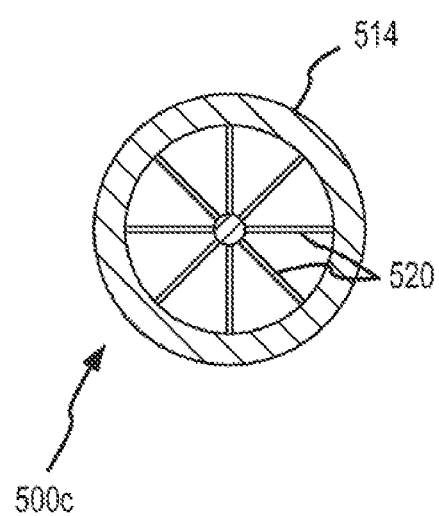

In FIG. 9*a*, the piezoelectric sensor 520 is provided on a support structure that can be thought of as the pole and metal frame of an umbrella, as better seen in FIG. 9*b*, the cross-sectional view taken along lines 9*b*-9*b*. In FIG. 9*c*, the piezoelectric sensor 520 is provided on a support structure that can be thought of as a spiral or ring mounted by a cross or T-bar to the pole portion, as better seen in FIG. 9*d*, the cross-sectional view taken along lines 9*d*-9*d*. In FIG. 9*e*, the piezoelectric sensor 520 is provided on a support structure that can be thought of as a combination of the umbrella frame in FIG. 9*a* and the cross or T-bar mounting in FIG. 9*c*, as can also be seen in FIG. 9*f*, the cross-sectional view taken along lines 9*f*-9*f*. Of course other shapes and configurations for supporting the piezoelectric sensor 520 are also contemplated, as will be readily apparent to those having ordinary skill in the art after becoming familiar with the teachings herein.

Figure 10A:
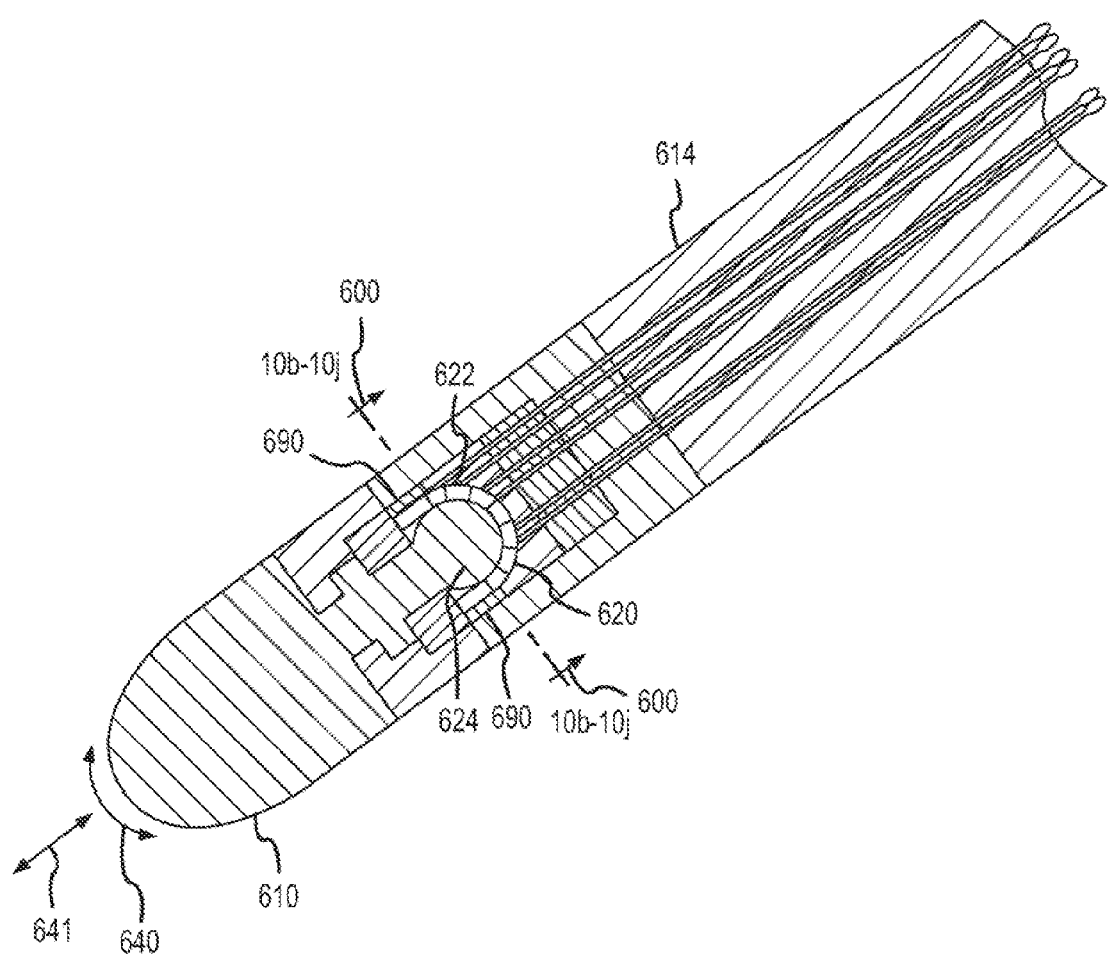
FIG. 10a is a cross-sectional view showing another alternative embodiment for operatively associating at least one piezoelectric sensor with an electrode.
Figure 10D:
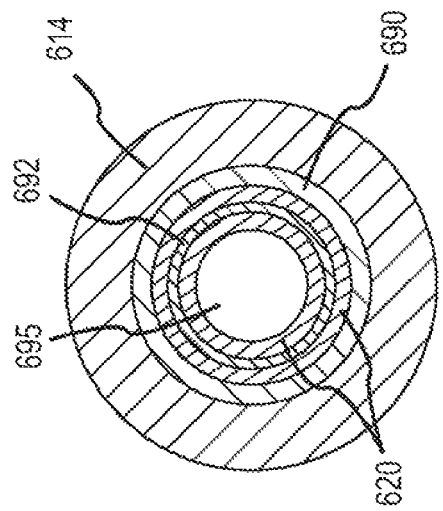
Figure 10C:
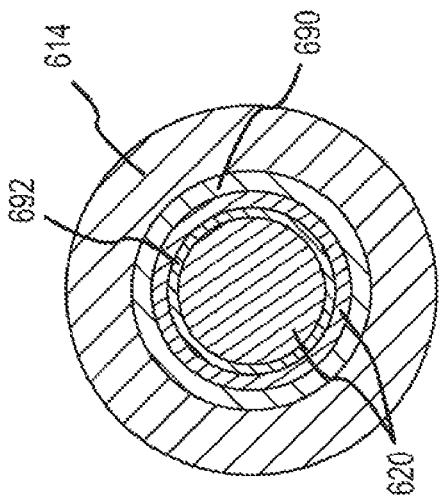

FIG. 10*a* is a cross-sectional view showing another alternative embodiment for operatively associating at least one piezoelectric sensor with an electrode. It is noted that 600-series reference numbers are used in the embodiments shown in FIG. 10*a* and FIG. 10*b-j* to refer to like elements described above with reference to FIGS. 2 and 2*a*. Therefore the description of some elements may not be repeated in the following discussion.

In each of these embodiments, the piezoelectric sensor 620 is provided on a half-spherical or "cups" shaped support structure 622 in contact with a substantially spherical or "ball" shaped neck portion 624 of the electrode 610. Contact of the electrode 610 with the target tissue causes the neck portion 624 of electrode 610 to move adjacent the "cup" shaped support structure 622, which in turn results in a stress or strain on the piezoelectric sensor 620. The piezoelectric sensor responds to these stresses on the electrode 610 by generating electrical (voltage or charge) signals. These electrical signals may be viewed by the user, e.g., as output on an electrical monitoring device.

It is noted that the neck portion 624 may be any suitable shape, such as, but not limited to the sphere or "ball" shape shown in FIG. 10*a*, an elliptical shape, rectangular shape, triangular shape, diamond shape, etc. Likewise, the "cup" shaped support structure 622 may be any suitable shape and does not necessarily have to compliment the neck portion 624. For example, the "cup" shaped support structure 622 in FIG. 10*a* compliments the sphere shaped neck portion 624, but the same "cup" shaped support structure 622 may also be used with a square shaped neck portion 624 (so that it behaves as a cam and engages the support structure 622).

Figure 10B:
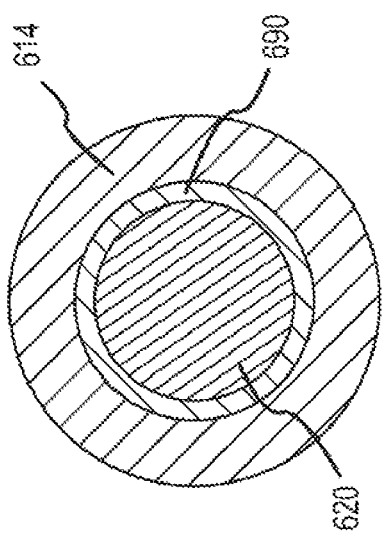
Figure 10G:
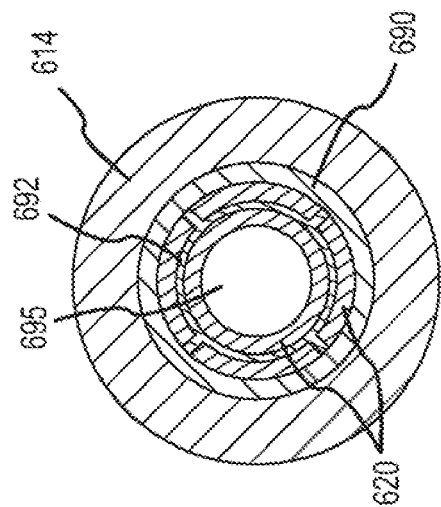
Figure 10F:
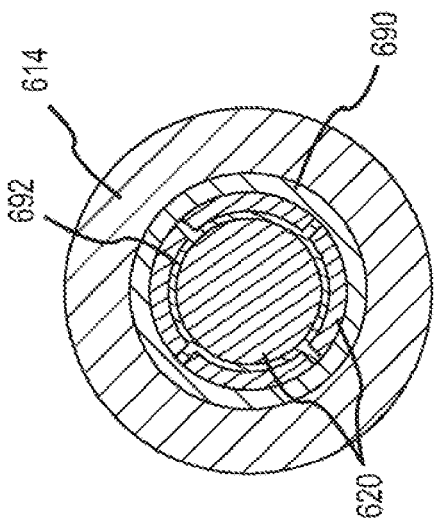
Figure 10E:
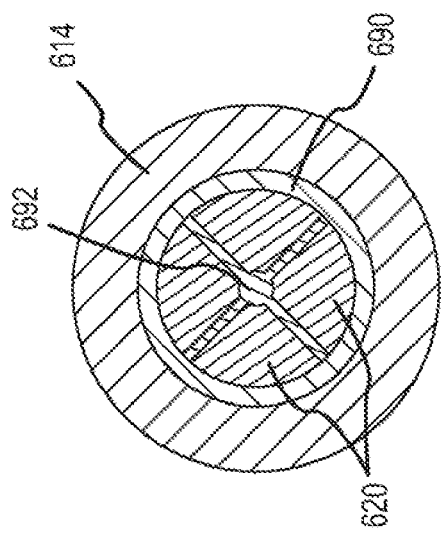
Figure 10J:
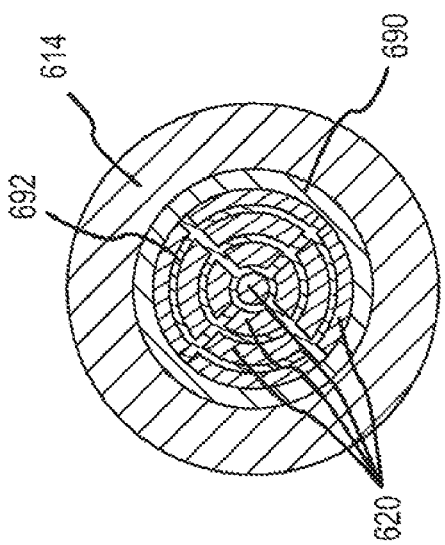
Figure 10I:
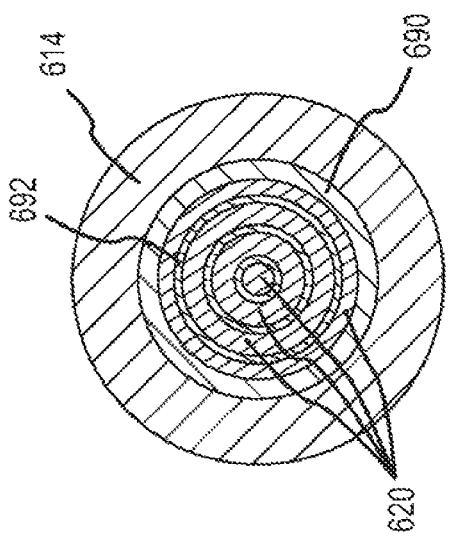
Figure 10H:
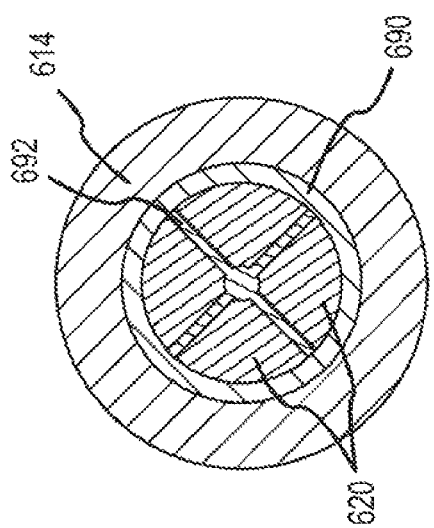

FIG. 10*b* is a cross-sectional view of the piezoelectric sensor 620 taken along lines 10*b*-10*j* in FIG. 10*a*, but for purposes of clarity, showing only the "cup" shaped support structure 622 without the neck portion 624. In FIG. 10*b*, the outer ring is the catheter 614, ring 690 is backing or support material also seen in FIG. 10a, and the center circle represents the piezoelectric sensor 620.

Optionally, the piezoelectric sensor 620 may be segmented. Segmenting the piezoelectric sensor 620 enables both axial and angular (or radial) stresses to be detected during operation. FIG. 10c-j are cross-sectional views showing alternative embodiments of the piezoelectric sensor 620 shown in FIG. 10a, wherein the piezoelectric sensor 620 is segmented. Again for purposes of clarity, only the "cup" shaped support structure 622 is shown without the neck portion 624 in FIG. 10c-j.

In FIG. 10c-j, the outer ring is the catheter 614, ring 690 is backing or support material also seen in FIG. 10a, and the center circle represents the piezoelectric sensor 620. Segmenting of the piezoelectric sensor 620 is referred to by reference number 692 in FIG. 10c-j. Similar segmentation may be applied on the embodiments of the sensors shown in FIG. 8a-h. Thus the segmentation 462 in FIG. 8a-b may have configuration such as shown in example FIG. 10b-j. In addition, in FIGS. 10d and 10g, lumen 695 formed through the piezoelectric sensor 620 may be provided for irrigated electrodes.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly, described. Changes in detail or structure, such as but not limited to combination of various aspects of the disclosed embodiments, may be made without departing from the spirit of the invention as defined in the appended claims.

What is claimed is:

1. A tissue contact sensing system that provides information indicative of contact between a tissue surface and a distal tip portion of an elongate member impinging upon the tissue surface, comprising:
   an elongate member having an intermediate section and a distal tip portion;
   a compliant material coupled between the intermediate section and the distal tip portion; and
   an electro-mechanical sensor means coupled to the compliant material for generating respective electrical signals in response to a mechanical load imposed on said electro-mechanical sensor means due to contact between a surface of tissue and said distal tip portion, wherein the electro-mechanical sensor means comprises at least three spaced-apart electro-mechanical sensors, the electro-mechanical sensors covered by an outer surface of the elongate member, and each of the electro-mechanical sensors being elongated having a longitudinal axis and arranged laterally adjacent one another in an elongated direction, the longitudinal axis of the sensors being substantially parallel to a longitudinal axis of the elongate member.

2. A system according to claim 1, wherein each of the electro-mechanical sensors is substantially equally spaced-apart from neighboring laterally adjacent sensors.

3. A system according to claim 1, wherein said electro-mechanical sensor means includes a common electrical reference.

4. A system according to claim 3, wherein said electro-mechanical sensor means are radially offset from adjacent electro-mechanical sensor means by between about 30 to about 180 degrees.

5. A system according to claim 1, wherein the elongate member comprises one of an electrophysiological catheter, a cardiovascular sheath or introducer device, and an intracardiac electrical lead.

6. A system according to claim 1, further comprising an active electrical component coupled to the distal portion of the elongate member.

7. A system according to claim 6, wherein the active electrical component comprises at least one of: an electrode, an ablation element, a temperature sensor.

8. A system according to claim 6, wherein the active electrical component comprises a means for ablating tissue.

9. A system according to claim 8, wherein the means for ablating tissue includes an electrode adapted to emit radiofrequency energy.

10. A system according to claim 1, wherein each of said at least three electro-mechanical sensors comprise a pair of spaced-apart electrically active plate members and one active plate of each said pair of spaced-apart electrically active plate members is one of electrically coupled to a common electrical reference and electrically coupled to an active plate member opposing the one active plate.

11. A system according to claim 1, wherein the electro-mechanical sensor means provides signals due to at least one of: a capacitive electrical effect, an inductive electrical effect, an inductive-capacitive effect, a resistive electrical effect and combinations thereof, between a pair of spaced electrically active plate members.

12. A system according to claim 1, further comprising a segmentation member disposed intermediate the at least three spaced-apart electro-mechanical sensors.

13. A system according to claim 1, further comprising an output device electrically connected to said electro-mechanical sensor means, the output device being adapted to receive the respective electrical signals and to calculate an indication of the magnitude and direction of the contact forces between the distal tip portion and the surface.

14. A system according to claim 13, wherein the output device is electrically connected to said electro-mechanical sensor means via a wireless telemetry link.

15. A system according to claim 1, wherein the compliant material comprises one of a resin-based material and any polymer containing alternate silicon and oxygen atoms, as $(-Si-O-Si-O-)_n$, whose properties are determined by the organic groups attached to the silicon atoms.

16. A system according to claim 1, wherein the compliant material comprises means for providing a deformable volume adjacent the electro-mechanical sensor means.

17. A system according to claim 1, wherein the at least three spaced-apart electro-mechanical sensors comprise a piezoelectric film material.

18. A system according to claim 1, further comprising an electrode coupled to the distal tip portion, and wherein the electro-mechanical sensor means couples to a support structure and the support structure couples to the electrode.

* * * * *